(12) United States Patent
Anderson et al.

(10) Patent No.: US 12,331,316 B2
(45) Date of Patent: Jun. 17, 2025

(54) T CELL WHICH EXPRESSES A GAMMA-DELTA T CELL RECEPTOR (TCR) AND A CHIMERIC ANTIGEN RECEPTOR (CAR)

(71) Applicant: UCL Business Ltd, London (GB)

(72) Inventors: John Anderson, London (GB); Jonathan Fisher, London (GB); Martin Pulé, London (GB); Kenth Gustafsson, London (GB)

(73) Assignee: UCL Business Ltd, London (GB)

( * ) Notice: Subject to any disclaimer, the term of this patent is extended or adjusted under 35 U.S.C. 154(b) by 541 days.

(21) Appl. No.: 17/528,836

(22) Filed: Nov. 17, 2021

(65) Prior Publication Data
US 2022/0211756 A1 Jul. 7, 2022

Related U.S. Application Data

(63) Continuation of application No. 15/567,165, filed as application No. PCT/GB2016/051235 on Apr. 29, 2016, now abandoned.

(30) Foreign Application Priority Data

Apr. 30, 2015 (GB) ...................... 1507368

(51) Int. Cl.
| | |
|---|---|
| A61K 40/31 | (2025.01) |
| A61K 40/11 | (2025.01) |
| A61K 40/42 | (2025.01) |
| A61P 31/04 | (2006.01) |
| A61P 31/12 | (2006.01) |
| A61P 35/00 | (2006.01) |
| C07K 14/725 | (2006.01) |
| C12N 5/0783 | (2010.01) |

(52) U.S. Cl.
CPC ............ *C12N 5/0638* (2013.01); *A61K 40/11* (2025.01); *A61K 40/31* (2025.01); *A61K 40/4202* (2025.01); *A61K 40/4258* (2025.01); *A61P 31/04* (2018.01); *A61P 31/12* (2018.01); *A61P 35/00* (2018.01); *C07K 14/7051* (2013.01); *C12N 5/0636* (2013.01); *A61K 2239/28* (2023.05); *A61K 2239/29* (2023.05); *C12N 2501/599* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 9,907,820 B2 | 3/2018 | Cooper et al. | |
| 10,881,688 B2 * | 1/2021 | Leek ...................... | A61P 31/10 |
| 2002/0107392 A1 | 8/2002 | Renhowe et al. | |
| 2014/0099309 A1 | 4/2014 | Powell, Jr. et al. | |
| 2015/0038684 A1 | 2/2015 | Jensen | |
| 2016/0175358 A1 | 6/2016 | Jakobovits et al. | |
| 2018/0125889 A1 | 5/2018 | Leek et al. | |
| 2018/0125890 A1 | 5/2018 | Anderson et al. | |

FOREIGN PATENT DOCUMENTS

| | | | |
|---|---|---|---|
| CA | 2 982 532 A | 11/2016 | |
| CN | 103492406 A | 1/2014 | |
| CN | 105158466 A | 12/2015 | |
| CN | 107771215 A | 3/2018 | |
| IL | 247208 | 12/2015 | |
| IL | 272264 | 12/2015 | |
| JP | 2002-535002 A | 10/2002 | |
| JP | 2003-529363 A | 10/2003 | |
| JP | 2008-509683 A | 4/2008 | |
| WO | WO 2006/006720 A1 | 1/2006 | |
| WO | WO 2008/152822 A1 | 12/2008 | |
| WO | WO 2012/079000 A1 | 6/2012 | |
| WO | WO-2013033626 A2 * | 3/2013 | ............ A61K 35/17 |
| WO | WO 2014/055657 A1 | 4/2014 | |
| WO | WO 2014/124143 | 8/2014 | |
| WO | WO 2014/130657 A | 8/2014 | |
| WO | WO 2014/153270 A1 | 9/2014 | |
| WO | WO 2014/186469 A2 | 11/2014 | |
| WO | WO 2015/017214 A1 | 2/2015 | |
| WO | WO 2015/066262 A1 | 5/2015 | |
| WO | WO 2015/075468 A1 | 5/2015 | |
| WO | WO-2015075470 A1 * | 5/2015 | ............ A61K 35/17 |
| WO | WO 2015/123642 A1 | 8/2015 | |
| WO | WO 2015/142675 A2 | 9/2015 | |
| WO | WO-2015132604 A1 * | 9/2015 | ............ A61K 35/17 |
| WO | WO 2015/164594 A1 | 10/2015 | |
| WO | WO 2016/005752 A1 | 1/2016 | |

(Continued)

OTHER PUBLICATIONS

Agrati et al., "Longitudinal characterization of dysfunctional T cell-activation during human acute Ebola infection," Cell Death and Disease, 7:1-8, (2016).
Saura-Esteller et al., "Gamma Delta T-Cell Based Cancer Immunotherapy: Past-Present-Future," Frontiers in Immunology, 13:1-11, (2022).
Schönefeldt et al., "The Diverse Roles of γδ T Cells in Cancer: From Rapid Immunity to Aggressive Lymphoma," 13:1-31, (2021).
Walker et al., "The T-Cell Response to HIV," Cold Spring Harbor Perspectives in Medicine, 2:1-19, (2012).
"TCRγ/δ+ T Cell Isolation Kit: human," Order No. 130-092-892, Miltenyi Biotec GmBH, 3 pages, (2007).
Bonneville and Scotet, "Human Vγ9Vδ2 T cells: promising new leads for immunotherapy of infections and tumors," Current Opinion in Immunology, 18:539-546, (2006).

(Continued)

*Primary Examiner* — Zachary S Skelding
(74) *Attorney, Agent, or Firm* — Alston & Bird LLP

(57) ABSTRACT

The present invention provides a T cell which expresses a gamma-delta T cell receptor (TCR) and a chimeric antigen receptor (CAR), wherein the CAR comprises: an antigen binding domain; a transmembrane domain; and a co-stimulatory intracellular signalling domain; wherein the intracellular signalling domain provides a co-stimulatory signal to the T cell following binding of antigen to the antigen binding domain.

10 Claims, 17 Drawing Sheets

Specification includes a Sequence Listing.

(56) References Cited

FOREIGN PATENT DOCUMENTS

| WO | WO 2016/166544 A1 | 10/2016 |
| WO | WO 2016/174461 A1 | 11/2016 |

OTHER PUBLICATIONS

Chan et al., "Differential CTLA-4 expression in human CD4+ versus CD8+ T cells is associated with increased NFAT1 and inhibition of CD4+ proliferation," Genes Immun., 15(1):25-32, (2014).

Chang et al., "Targeting the programmed cell death 1: programmed cell death ligand 1 pathway reverses T cell exhaustion in patients with sepsis," Critical Care, 18:R3, 15 pages, (2014).

Chmielewski et al., "T cells redirected by a CD3ζ chimeric antigen receptor can establish self-antigen-specific tumour protection in the long term," Gene therapy, 20:177-186, (2013).

Database WPI Thomson, "Pharmaceutical, contains (gamma) delta T cell and monoclonal antibody therapeutic agent," Thomson Scientific, London, GB XP002745229, 3 pages, (2009).

Deniger et al., "Bispecific T-cells Expressing Polyclonal Repertoire of Endogenous γδ T-cell Receptors and Introduced CD19-specific Chimeric Antigen Receptor," The American Society of Gene & Cell Therapy, 21(3):638-647, (2013).

Deniger et al., "Clinical applications of gamma delta T cells with multivalent immunity," Frontiers in Immunology 5(636), 1-10, (2014).

Farnault et al., "Clinical evidence implicating gamma-delta T cells in EBV control following cord blood transplantation," Bone Marrow Transplant., 48(11):1478-1479, (2013).

Fedorov et al., "PD-1- and CTLA-4-Based Inhibitory Chimeric Antigen Receptors (iCARs) Divert Off-Target Immunotherapy Responses," Sci. Transl. Med., 5(215):215ra172, 25 pages, (2013).

Fisher, J. et al., "Avoidance of On-Target Off-Tumor Activation Using a Co-stiumlation-Only Chimeric Antigen Receptor," Molecular Therapy, 1234-1247, (May 3, 2017).

Fournie et al., "What lessons can be learned from γδ T cell-based cancer immunotherapy trials?," Cellular & Molecular Immunology, 10:35-41, (2013).

Garcia et al., "IL-15 Enhances the Response of Human γδ T Cells to Nonpeptide Microbial Antigens," J. Immunol., 160:4322-4329, (1998).

Haque et al., "Allogeneic cytotoxic T-cell therapy for EBV-positive posttransplantation lymphoproliferative disease: results of a phase 2 multicenter clinical trial," Blood, 110(4):1123-1131, (2007).

Harly et al., "Molecules and mechanisms implicated in the peculiar antigenic activation process of human Vγ9Vδ2 T cells," Frontiers in Immunology, 5(657):1-13, (2015).

Imai et al., "Genetic modification of primary natural killer cells overcomes inhibitory signals and induces specific killing of leukemic cells," Blood, 106(1):376-383 (2005).

Ivanov et al., "Role of Non-Conventional T Lymphocytes in Respiratory Infections: the Case of the Pneumococcus," PLOS Pathogens, 10(10):e1004300, 11 pages, (2014).

Iwasaki et al., "Expression and function of PD-1 in human γδ T cells that recognize phosphoantigens," Eur. J. Immunol., 41:345-355, (2011).

Kalwak et al., "CIK cell and γδ T cell expansion in cultures of patients with neuroblastoma X and of healthy potential haploidentical haematopoietic cell donors," Onkol. Pol, 8(2):49-55, (2005). [Abstract only; p. 2].

Knight et al., "Human Vdelta1 gamma-delta T cells exert potent specific cytotoxicity against primary multiple myeloma cells," Cytotherapy, 14:1110-1118, (2012).

Kowolik et al., "CD28 Costimulation Provided through a CD19-Specific Chimeric Antigen Receptor Enhances In vivo Persistence and Antitumor Efficacy of Adoptively Transferred T Cells," Cancer Res., 66(22):10995-11004, (2006).

Krause et al., "Antigen-dependent CD28 Signaling Selectively Enhances Survival and Proliferation in Genetically Modified Activated Human Primary T Lymphocytes," J. Exp. Med., 188(4):619-626, (1998).

Kunzmann et al., "Simulation of γδ T cells by aminobisphosphonates and induction of antiplasma cell activity in multiple myeloma," Blood, 96(2), 9 pages, (2000).

Locatelli et al., "At the Bedside: Innate immunity as an immunotherapy tool for hematological malignancies," Journal of Leukocyte Biology, 94:1141-1157, (2013).

Long et al., "4-1BB costimulation ameliorates T cell exhaustion induced by tonic signaling of chimeric antigen receptors," Nature Medicine, 21(6), 13 pages, (2015).

Meraviglia et al., "In vivo manipulation of Vγ9Vδ2 T cells with zoledronate and low-dose interleukin-2 for immunotherapy of advanced breast cancer patients," Clin Exp Immunol., 161(2):290-297, (2010).

Nakazawa et al., "Cytotoxic human peripheral blood-derived γδ T cells kill glioblastoma cell lines: implications for cell-based immunotherapy for patients with glioblastoma," J Neurooncol, 116:31-39, (2014).

Nedellec et al., "NKG2D Costimulates Human Vγ9Vδ2 T Cell Antitumor Cytotoxicity through Protein Kinase CΘ-Dependent Modulation of Early TCR-Induced Calcium and Transduction Signals," J. Immunol., 185:55-63, (2010).

Nicol et al., "Clinical evaluation of autologous gamma delta T cell-based immunotherapy for metastatic solid tumours," Br J Cancer, 105(6):778-786, (2011).

Noguchi et al., "Zoledronate-activated Vγ9γδ T cell-based immunotherapy is feasible and restores the impairment of gamma-delta T cells in patients with solid tumors," Cytotherapy, 13:92-97, (2011).

Nussbaumer et al., "Essential requirements of zoledronate-induced cytokine and γδ T cell proliferative responses," J. Immunol., 191(3):1345-1355, (2013).

Pistoia et al., "Immunosuppressive microenvironment in neuroblastoma," Front. Oncol., 3(167):1-8, (2013).

Pizzitola et al., "In Vitro Comparison of Three Different Chimeric Receptor-modified Effector T-cell Populations for Leukemia Cell Therapy," J Immunother, 34(6):469-479, (2011).

Ribot et al., "B7-CD28 Costimulatory Signals Control the Survival and Proliferation of Murine and Human γδ T Cells via IL-2 Production," J. Immunol., 189:1202-1208, (2012).

Sadelain et al., "The Basic Principles of Chimeric Antigen Receptor Design," Cancer Discovery, 3(4):388-398, (2013).

Sakamoto et al., "Adoptive Immunotherapy for Advanced Non-small Cell Lung Cancer Using Zoledronate-expanded γδ T Cells: A Phase I Clinical Study," J. Immunother., 34(2):202-211, (2011).

Santolaria et al., "Repeated Systemic Administrations of Both Aminobisphosphonates and Human V γ9Vδ2 T Cells Efficiently Control Tumor Development In Vivo," J. Immunol., 191:1993-2000, (2013).

Shi et al., "Chimeric antigen receptor for adoptive immunotherapy of cancer: latest research and future prospects," Molecular Cancer, 13:219, (2014).

Singh et al., "Reprogramming CD19-Specific T Cells with IL-21 Signaling Can Improve Adoptive Immunotherapy of B-Lineage Malignancies," Cancer Res., 71(10):3516-3527, (2011).

Suzuki et al., "Disialoganglioside GD2 as a therapeutic target for human diseases," Expert Opinion on Therapeutic Targets, 19(3):349-362, (2015).

Tanaka et al., "Natural and synthetic non-peptide antigens recognized by human γδ T cells," Nature, 375(6527):155-158, (1995).

Thompson et al., "Activation of γδ T Cells by Bisphosphonates," Osteoimmunoligy, Advances in Experimental Medicine and Biology, Ed. Y. Choi, 658:11-20, (2010).

Tu et al., "The aminobisphosphonate pamidronate controls influenza pathogenesis by expanding a γδ T cell population in humanized mice," J Exp Med., 208(7):1511-1522, (2011).

Vanderstegen et al., "The pharmacology of second-generation chimeric antigen receptors," Nature Reviews, Drug Discovery, 14:499-509, (2015).

(56) References Cited

OTHER PUBLICATIONS

Vanseggelen et al., "On-target off-tumor toxicity; when enhancing an NKG2D-based CAR in vitro led to severe toxicities in vivo," Journal for Immunotherapy, 2(Suppl 3):P15, (2014).
Vantourout and Hayday, "Six-of-the-best: unique contributions of γδ T cells to immunology," Nature, 13:88-100, (2013).
Wallace et al., "γδ T lymphocyte responses to HIV," Clin Exp Immunol., 103(2):177-184, (1996).
Wang et al., "Indirect Stimulation of Human Vγ2Vδ2 T Cells through Alterations in Isoprenoid Metabolism," J. Immunol., 187:5099-5113, (2011).
Wilhelm et al., "Successful adoptive transfer and in vivo expansion of haploidentical γδ T cells," Journal of Translational Medicine, 12(45), 5 pages, (2014).
Wu et al., "An Activating Immunoreceptor Complex Formed by NKG2D and DAP10," Science, 285(5428):730-732, (1999).
Wu et al., "γδ T Cells and Their Potential for Immunotherapy," Int. J. Biol. Sci., 10:119-135, (2014).
Xiang et al., "Targeted activation of human Vγ9Vδ2-T cells controls epstein-barr virus-induced B cell lymphoproliferative disease," Cancer Cell, 26(4):565-576, (2014).
Xu et al. "Mitogen-activated protein kinase-activated protein kinase 2 regulates tumor necrosis factor-induced interleukin-6 expression via human antigen R," Chin Med J. 126(22):4322-4326, (2013).
Zhao and Gao, "Research progress of CAR T-cell in tumor therapy," Chin J Clin Oncol, 42(3):190-194, (2015).
China National Intellectual Property Administration, CN Office Action for Patent Application No. 201680034862.3, dispatched Aug. 2, 2021.
EP 16720532.7 Examination Report mailed Mar. 13, 2019.
EP Application No. 16 720 532.7, Office Action mailed Mar. 12, 2021.
European Patent Office, EP Application No. 16720532.7, dated Mar. 12, 2021.
Japanese Patent Office, JP Notice Reasons for Refusal for JP Patent Application No. 2017-554350, dispatched Feb. 9, 2021.
Japanese Patent Office, JP Patent Application No. 2017-554035 Notice of Refusal, dispatched Jan. 26, 2021.
U.S. Application No. 15/567, 165, Non-Final Office Action mailed Jan. 3, 2020.
U.S. Application No. 15/576, 165, Final Office Action mailed Oct. 21, 2020.
WIPO Application No. PCT/GB2015/051985, PCT International Preliminary Report on Patentability issued Jan. 10, 2017.
WIPO Application No. PCT/GB2015/051985, PCT International Search Report and Written Opinion of the International Searching Authority mailed Oct. 12, 2015.
WIPO Application No. PCT/GB2016/051050, PCT International Preliminary Report on Patentability issued Oct. 19, 2017.
WIPO Application No. PCT/GB2016/051050, PCT International Search Report and Written Opinion of the International Searching Authority mailed Jun. 22, 2016.
WIPO Application No. PCT/GB2016/051235, PCT International Preliminary Report on Patentability issued Oct. 31, 2017.
WIPO Application No. PCT/GB2016/051235, PCT International Search Report mailed Jun. 29, 2016.
WIPO Application No. PCT/GB2016/051235, PCT Written Opinion of the International Searching Authority mailed Jun. 29, 2016.
European Patent Office, EP Application No. 15745544.5, dated Dec. 21, 2021.
Salot et al., "Large scale expansion of γ9δ2 T lymphocytes: Innacell γδ™ cell therapy product," Journal of Immunological Methods, 326:63-75, (2007).
Mitani et al., "Usefulness of HLA DNA typing in Unattainable Cases for Histocompatibility Testing in Allogeneic Bone Marro Transplantation," Japanese Journal of Transfusion Medicine, 39(5):806-813, (1993).
"HLA", Pathological and Clinical, 16(6):711-716, (1998).
Canadian Patent Office, CA Patent Application No. 2,982,523 Office Action, dispatched Apr. 1, 2022.
Japanese Patent Office, JP Patent Application No. 2020-115432 Office Action, dispatched Jun. 9, 2022.

* cited by examiner

Error bars denote SEM for n=3-6 independent donors

*Nucleotide sequence of the aGD2-Fc-DAP10 CAR (SEQ ID NO: 5)*

ATGGAGACCGACACCCTGCTGCTGTGGGTGCTGCTGCTGTGGGTGCCA
GGCAGCACCGGCCAGGTGCAGCTGCAGGAGTCTGGCCCAGGCCTGGT
GAAGCCCAGCCAGACCCTGAGCATCACCTGCACCGTGAGCGGCTTCAG
CCTGGCCAGCTACAACATCCACTGGGTGCGGCAGCCCCCAGGCAAGGG
CCTGGAGTGGCTGGGCGTGATCTGGCTGGCGGCAGCACCAACTACAA
CAGCGCCCTGATGAGCCGGCTGACCATCAGCAAGGACAACAGCAAGAA
CCAGGTGTTCCTGAAGATGAGCAGCCTGACAGCCGCCGACACCGCCGT
GTACTACTGCGCCAAGCGGAGCGACGACTACAGCTGGTTCGCCTACTG
GGGCCAGGGCACCCTGGTGACCGTGAGCTCTGGCGGAGGCGGCTCTG
GCGGAGGCGGCTCTGGCGGAGGCGGCAGCGAGAACCAGATGACCCAG
AGCCCCAGCAGCTTGAGCGCCAGCGTGGGCGACCGGGTGACCATGACC
TGCAGAGCCAGCAGCAGCGTGAGCAGCAGCTACCTGCACTGGTACCAG
CAGAAGAGCGGCAAGGCCCCAAAGGTGTGGATCTACAGCACCAGCAAC
CTGGCCAGCGGCGTGCCCAGCCGGTTCAGCGGCAGCGGCAGCGGCAC
CGACTACACCCTGACCATCAGCAGCCTGCAGCCCGAGGACTTCGCCAC
CTACTACTGCCAGCAGTACAGCGGCTACCCCATCACCTTCGGCCAGGGC
ACCAAGGTGGAGATCAAGCGGTCGGATCCCGCCGAGCCCAAATCTCCT
GACAAAACTCACACATGCCCACCGTGCCCAGCACCTCCCGTGGCCGGC
CCGTCAGTCTTCCTCTTCCCCCCAAAACCCAAGGACACCCTCATGATCG
CCCGGACCCCTGAGGTCACATGCGTGGTGGTGGACGTGAGCCACGAAG
ACCCTGAGGTCAAGTTCAACTGGTACGTGGACGGCGTGGAGGTGCATAA
TGCCAAGACAAAGCCGCGGGAGGAGCAGTACAACAGCACGTACCGTGT
GGTCAGCGTCCTCACCGTCCTGCACCAGGACTGGCTGAATGGCAAGGA
GTACAAGTGCAAGGTCTCCAACAAAGCCCTCCCAGCCCCCATCGAGAAA
ACCATCTCCAAAGCCAAAGGGCAGCCCCGAGAACCACAGGTGTACACC
CTGCCCCCATCCCGGGATGAGCTGACCAAGAACCAGGTCAGCCTGACC
TGCCTGGTCAAAGGCTTCTATCCAGCGACATCGCCGTGGAGTGGGAG
AGCAATGGGCAACCGGAGAACAACTACAAGACCACGCCTCCCGTGCTG
GACTCCGACGGCTCCTTCTTCCTCTACAGCAAGCTCACCGTGGACAAGA
GCAGGTGGCAGCAGGGGAACGTCTTCTCATGCTCCGTGATGCATGAGG
CCCTGCACAATCACTATACCCAGAAATCTCTGAGTCTGAGCCCAGGCAA
GAAGGACCCCAAGTTCTGGGTCCTGGTGGTGGTGGGAGGCGTGCTGGC
CTGTTACTCTCTCCTGGTGACCGTGGCCTTCATCATCTTCTGGGTGTGC
GCCAGACCACGGCGGAGCCCAGCCCAGGAGGACGGCAAGGTGTACAT
CAACATGCCCGGCCGCGGCTGA

*Amino acid sequence of the aGD2-Fc-DAP10 CAR (SEQ ID NO: 2)*

METDTLLLWVLLLWVPGSTGQVQLQESGPGLVKPSQTLSITCTVSGFSLAS
YNIHWVRQPPGKGLEWLGVIWAGGSTNYNSALMSRLTISKDNSKNQVFLKM
SSLTAADTAVYYCAKRSDDYSWFAYWGQGTLVTVSSGGGGSGGGGSGGG
GSENQMTQSPSSLSASVGDRVTMTCRASSSVSSSYLHWYQQKSGKAPKV
WIYSTSNLASGVPSRFSGSGSGTDYTLTISSLQPEDFATYYCQQYSGYPITF
GQGTKVEIKRSDPAEPKSPDKTHTCPPCPAPPVAGPSVFLFPPKPKDTLMIA
RTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRD

FIG. 10

ELTKNQVSLTCLVKGFYPSDIAVEWESNGQPENNYKTTPPVLDSDGSFFLY
SKLTVDKSRWQQGNVFSCSVMHEALHNHYTQKSLSLSPGKKDPKFWVLVV
VGGVLACYSLLVTVAFIIFWVCARPRRSPAQEDGKVYINMPGRG

Key anti-GD2 scFV
CH2CH3 spacer with PPVA mutation to prevent binding to Fcγ receptors
CD28 transmembrane domain
DAP10 endodomain FIG. 10 (Continued)

*Nucleotide sequence of the aCD33-Fc-DAP10 CAR (SEQ ID NO: 4)*

```
ATGGCCGTGCCCACTCAGGTCCTGGGGTTGTTGCTACTGTGGCTTACAG
ATGCCAGATGTGACATCCAGATGACACAGTCTCCATCTTCCCTGTCTGCA
TCTGTCGGAGATCGCGTCACCATCACCTGTCGAGCAAGTGAGGACATTT
ATTTTAATTTAGTGTGGTATCAGCAGAAACCAGGAAAGGCCCCTAAGCTC
CTGATCTATGATACAAATCGCTTGGCAGATGGGGTCCCATCACGGTTCA
GTGGCTCTGGATCTGGCACACAGTATACTCTAACCATAAGTAGCCTGCA
ACCCGAAGATTTCGCAACCTATTATTGTCAACACTATAAGAATTATCCGCT
CACGTTCGGTCAGGGGACCAAGCTGGAAATCAAAGATCTGGTGGCGG
AGGGTCAGGAGGCGGAGGCAGCGGAGGCGGTGGCTCGGGAGGCGGA
GGCTCGAGATCTGAGGTGCAGTTGGTGGAGTCTGGGGGCGGCTTGGTG
CAGCCTGGAGGGTCCCTGAGGCTCTCCTGTGCAGCCTCAGGATTCACTC
TCAGTAATTATGGCATGCACTGGATCAGGCAGGCTCCAGGGAAGGGTCT
GGAGTGGGTCTCGTCTATTAGTCTTAATGGTGGTAGCACTTACTATCGAG
ACTCCGTGAAGGGCCGATTCACTATCTCCAGGGACAATGCAAAAGCAC
CCTCTACCTTCAAATGAATAGTCTGAGGGCCGAGGACACGGCCGTCTAT
TACTGTGCAGCACAGGACGCTTATACGGGAGGTTACTTTGATTACTGGG
GCCAAGGAACGCTGGTCACAGTCTCGTCTATGGATCCGCCGAGCCCA
AATCTCCTGACAAAACTCACACATGCCCACCGTGCCCAGCACCTCCCGT
GGCCGGCCCGTCAGTCTTCCTCTTCCCCCCAAAACCCAAGGACACCCTC
ATGATCGCCCGGACCCCTGAGGTCACATGCGTGGTGGTGGACGTGAGC
CACGAAGACCCTGAGGTCAAGTTCAACTGGTACGTGGACGGCGTGGAG
GTGCATAATGCCAAGACAAAGCCGCGGGAGGAGCAGTACAACAGCACG
TACCGTGTGGTCAGCGTCCTCACCGTCCTGCACCAGGACTGGCTGAATG
GCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGT
GTACACCCTGCCCCCATCCCGGGATGAGCTGACCAAGAACCAGGTCAG
CCTGACCTGCCTGGTCAAAGGCTTCTATCCCAGCGACATCGCCGTGGAG
TGGGAGAGCAATGGGCAACCGGAGAACAACTACAAGACCACGCCTCCC
GTGCTGGACTCCGACGGCTCCTTCTTCCTCTACAGCAAGCTCACCGTGG
ACAAGAGCAGGTGGCAGCAGGGGAACGTCTTCTCATGCTCCGTGATGC
ATGAGGCCCTGCACAATCACTATACCCAGAAATCTCTGAGTCTGAGCCC
AGGCAAGAAGGACCCCAAGTTCTGGGTCCTGGTGGTGGTGGGAGGCGT
GCTGGCCTGTTACTCTCTCCTGGTGACCGTGGCCTTCATCATCTTCTGG
GTGTGCGCCAGACCACGGCGGAGCCCAGCCCAGGAGGACGGCAAGGT
GTACATCAACATGCCCGGCCGCGGCTGA
```

*Amino acid sequence of the aCD33-Fc-DAP10 CAR (SEQ ID NO: 1)*

```
MAVPTQVLGLLLLWLTDARCDIQMTQSPSSLSASVGDRVTITCRASEDIYFN
LVWYQQKPGKAPKLLIYDTNRLADGVPSRFSGSGSGTQYTLTISSLQPEDFA
TYYCQHYKNYPLTFGQGTKLEIKRSGGGGSGGGGSGGGGSRSEV
QLVESGGGLVQPGGSLRLSCAASGFTLSNYGMHWIRQAPGKGLEWVSSIS
LNGGSTYYRDSVKGRFTISRDNAKSTLYLQMNSLRAEDTAVYYCAAQDAYT
GGYFDYWGQGTLVTVSSMDPAEPKSPDKTHTCPPCPAPPVAGPSVFLFPP
KPKDTLMIARTPEVTCVVVDVSHEDPEVKFNWYVDGVEVHNAKTKPREEQY
NSTYRVVSVLTVLHQDWLNGKEYKCKVSNKALPAPIEKTISKAKGQPREPQV
```

FIG. 11

YTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGKKD
PKFWVLVVVGGVLACYSLLVTVAFIIFWVCARPRRSPAQEDGKVYINMPGR
G

*Key* anti-CD33 scFV
CH2CH3 spacer with PPVA mutation to prevent binding to FcX receptors
CD28 transmembrane domain
DAP10 endodomain FIG. 11 (Continued)

T CELL WHICH EXPRESSES A GAMMA-DELTA T CELL RECEPTOR (TCR) AND A CHIMERIC ANTIGEN RECEPTOR (CAR)

CROSS-REFERENCE TO RELATED APPLICATIONS

This application is a continuation of U.S. application Ser. No. 15/567,165, filed Oct. 27, 2017, which is a US National Stage entry of International Application No. PCT/GB2016/051235 filed Apr. 29, 2016, which claims the benefit of GB Application No. 1507368.7, filed Apr. 30, 2015, each of which is herein incorporated by reference in its entirety for all purposes.

REFERENCE TO A SEQUENCE LISTING SUBMITTED AS A TEXT FILE VIA EFS WEB

The Sequence Listing written in file 507912SEQLIST.txt is 35 kb, was created on Nov. 16, 2021, and is hereby incorporated by reference.

FIELD OF THE INVENTION

The present invention relates to immunotherapeutic T cells. In particular, the invention provides immunotherapeutic gamma-delta T cells comprising a chimeric antigen receptor (CAR).

BACKGROUND TO THE INVENTION

Chimeric antigen receptors (CARs) developed for cancer immunotherapy combine an extracellular antigen recognition domain with signalling domains specific for effector cells within a single molecule. The most common CAR system involves an antigen recognition domain derived from a monoclonal antibody fused to signalling domains which provide activating signals for T cells.

Typically, the signalling domains of a CAR provides cytotoxicity, proliferation and survival signals to activate the effector cell upon binding of antigen to the antigen recognition domain (Signals 1 and 2).

A limitation of this technology is potential 'on target-off tumour toxicity'. This toxicity is caused by the recognition of low levels of a cancer-associated antigen recognised by a CAR on normal tissues. For instance GD2 is a target for neuroblastoma but also is expressed on nerves; and PSMA is a target for prostate cancer cells but is also found on normal kidney, liver and colon cells, and brain astrocytes. This problem is more profound in solid tumours where there is a dearth of highly selective targets.

Thus there is a need for cancer immunotherapies which address the above problems.

SUMMARY OF ASPECTS OF THE INVENTION

The present inventors have determined a mechanism of reducing 'on target-off tumour toxicity' by using CARs in gamma delta (γδ) T-cells. In the system described herein, a CAR is used to provide a co-stimulatory signal (signal 2) to a γδ T-cell upon binding of antigen to the antigen recognition domain of the CAR. In this way, signal 2 is only provided to the T-cell upon binding of the CAR to its target antigen (FIG. 2A). Signal 1 for γδ T-cell activation is provided by the endogenous TCR, which is activated by danger signals, such as phosphoantigens.

A γδ T-cell requires both signal 1 and signal 2 for optimal effector function. Thus, in the present system the γδ T-cell will only be fully activated for cytotoxicity, proliferation and cytokine secretion if the target cell: (i) expresses the antigen recognised by the CAR; and (ii) expresses danger signals recognised by the endogenous γδ TCR.

Thus, in a first aspect the present invention provides a T cell which expresses a gamma-delta T cell receptor (TCR) and a chimeric antigen receptor (CAR), wherein the CAR comprises;
  (i) an antigen binding domain;
  (ii) a transmembrane domain; and
  (iii) a co-stimulatory intracellular signalling domain;
wherein the intracellular signalling domain provides a co-stimulatory signal to the T cell following binding of antigen to the antigen binding domain.

As such, binding of a first antigen to the γδ TCR results in signal 1 production and binding of a second antigen to the antigen binding domain of the CAR results in signal 2 production.

The antigen binding domain may be capable of binding to a tumour-associated antigen (TAA).

The antigen binding domain may be capable of binding to GD2, CD33, CD19 or EGFR.

The intracellular signalling domain may comprise the DAP10, CD28, CD27, 41BB, OX40, CD30, IL2-R, IL7-R, IL21-R, NKp30, NKp44 or DNAM-1 (CD226) signalling domain.

The transmembrane domain of the CAR may comprise a CD8 stalk or a CD28 transmembrane domain.

The intracellular signalling domain of the CAR may comprise the DAP10 signalling domain.

The CAR may further comprise a spacer domain between the antigen binding domain and the transmembrane domain.

The γδ TCR may be capable of binding to a phosphoantigen/butyrophilin 3A1 complex; major histocompatibility complex class I chain-related A (MICA); major histocompatibility complex class I chain-related B (MICB); NKG2D ligand 1-6 (ULBP 1-6); CD1c; CD1d; endothelial protein C receptor (EPCR); lipohexapeptides; phycoreythrin or histidyl-tRNA-synthase.

The CAR may comprise one of the following amino acid sequences:

```
(aCD33-Fc-DAP10 CAR)
                                SEQ ID NO: 1
MAVPTQVLGLLLLWLTDARCDIQMTQSPSSLSASV

GDRVTITCRASEDIYFNLVWYQQKPGKAPKLLIY

DTNRLADGVPSRFSGSGSGTQYTLTISSLQPEDFA

TYYCQHYKNYPLTFGQGTKLEIKRSGGGGSGGGGS

GGGGSGGGGSRSEVQLVESGGGLVQPGGSLRLSCA

ASGFTLSNYGMHWIRQAPGKGLEWVSSISLNGGS

TYYRDSVKGRFTISRDNAKSTLYLQMNSLRAEDTA

VYYCAAQDAYTGGYFDYWGQGTLVTVSSMDPAEPK

SPDKTHTCPPCPAPPVAGPSVFLFPPKPKDTLMIA

RTPEVTCVVVDVSHEDPEVKFNVVYVDGVEVHNAK

TKPREEQYNSTYRVVSVLTVLHQDWLNGKEYKCKV

SNKALPAPIEKTISKAKGQPREPQVYTLPPSRDEL
```

```
                      -continued
TKNQVSLTCLVKGFYPSDIAVEWESNGQPENNYKT

TPPVLDSDGSFFLYSKLTVDKSRWQQGNVFSCSVM

HEALHNHYTQKSLSLSPGKKDPKFWVLVVVGGVL

ACYSLLVTVAFIIFWVCARPRRSPAQEDGKVYIN

MPGRG (aGD2-Fc-DAP10 CAR)
                                     SEQ ID NO: 2
METDTLLLWVLLLWVPGSTGQVQLQESGPGLVK

PSQTLSITCTVSGFSLASYNIHWVRQPPGKGLEW

LGVIWAGGSTNYNSALMSRLTISKDNSKNQVFLKM

SSLTAADTAVYYCAKRSDDYSWFAYWGQGTLVTVS

SGGGGSGGGGSGGGGSENQMTQSPSSLSASVGDRV

TMTCRASSSVSSSYLHVVYQQKSGKAPKVWIYSTS

NLASGVPSRFSGSGSGTDYTLTISSLQPEDFATYY

CQQYSGYPITFGQGTKVEIKRSDPAEPKSPDKTHT

CPPCPAPPVAGPSVFLFPPKPKDTLMIARTPEVTC

VVVDVSHEDPEVKFNVVYVDGVEVHNAKTKPREEQ

YNSTYRVVSVLTVLHQDWLNGKEYKCKVSNKALPA

PIEKTISKAKGQPREPQVYTLPPSRDELTKNQVSL

TCLVKGFYPSDIAVEWESNGQPENNYKTTPPVLDS

DGSFFLYSKLTVDKSRWQQGNVFSCSVMHEALHNH

YTQKSLSLSPGKKDPKFWVLVVVGGVLACYSLLV

TVAFIIFWVCARPRRSPAQEDGKVYINMPGRG
```

In a further aspect the present invention provides a CAR comprising; (i) an antigen-binding domain; (ii) a transmembrane domain; and (iii) an intracellular signalling domain; wherein the intracellular signalling domain comprises a co-stimulatory intracellular signalling domain but does not comprise a CD3 endodomain.

The co-stimulatory intracellular signalling domain may be selected from a DAP10, CD28, CD27, 41 BB, OX40, CD30, IL2-R, IL7-R, IL21-R, NKp30, NKp44 or DNAM-1 (CD226) signalling domain.

In a second aspect the present invention provides a CAR comprising, an antigen-binding domain; a transmembrane domain; and an intracellular signalling domain; wherein the intracellular signalling domain comprises a DAP10 signalling domain. The intracellular signalling domain may consist of or consist essentially of a DAP10 signalling domain.

In a particular embodiment the intracellular signalling domain of the CAR according to the second aspect of the invention does not comprise a CD3 endodomain.

The CAR according to the second aspect of the invention may be a CAR as defined in the first aspect of the invention.

In a third aspect the present invention provides a nucleic acid sequence encoding a CAR as defined in the first or second aspects of the invention.

In a fourth aspect the present invention provides a vector comprising a nucleic acid sequence as defined by the third aspect of the invention.

The vector may be a retroviral vector, a lentiviral vector or a transposon.

In a fifth aspect the present invention relates to method for making a cell according to the first aspect of the invention, which comprises the step of introducing: a nucleic acid sequence according to the third aspect of the invention or a vector according to fourth aspect of the invention into a cell.

The method may comprise the step of stimulating the cell with a gamma delta T cell stimulating agent.

The γδ T cell stimulating agent may be selected from, for example, isopentenyl pyrophosphate (IPP); analogs of IPP such as bromohydrin pyrophosphate and (E)-4-Hydroxy-3-methyl-but-2-enyl pyrophosphate; and inhibitors of farnesyl pyrophosphate synthase (FPPS) such as aminobisphosphonates (e.g. zoledronate or pamidronate).

The cell may be from a sample isolated from a subject.

In a sixth aspect the present invention provides a pharmaceutical composition comprising a cell according to the first aspect of the present invention.

In a seventh aspect the present invention relates to a method for treating a disease, which comprises the step of administering a pharmaceutical composition according to the sixth aspect of the invention to a subject.

The method may comprise the step of administering a γδ T cell stimulating agent to the subject.

The γδ T cell stimulating agent may be selected from, for example, isopentenyl pyrophosphate (IPP); analogs of IPP such as bromohydrin pyrophosphate and (E)-4-Hydroxy-3-methyl-but-2-enyl pyrophosphate; and inhibitors of farnesyl pyrophosphate synthase (FPPS) such as aminobisphosphonates (e.g. zoledronate or pamidronate).

The method may comprise the following steps:
(i) isolation of a cell-containing sample from a subject;
(ii) transduction or transfection of cells with: a nucleic acid sample according to the third aspect of the present invention or a vector according to the fourth aspect of the present invention; and
(iii) administering the cells from (ii) to the subject.

In an eighth aspect the present invention relates to a pharmaceutical composition according to the sixth aspect of the present invention for use in treating a disease.

In a ninth aspect the present invention relates to the use of a cell according to the first aspect of the present invention in the manufacture of a medicament for treating and/or preventing a disease.

The disease described herein may be cancer, microbial infection or viral infection.

The present invention therefore provides a γδ T cell which is only fully activated by, and therefore capable of killing, a target cell which expresses a first antigen which is capable of binding to the endogenous γδ TCR (and thus stimulating productive signal 1) and a second antigen which is capable of binding to the CAR (and thus stimulating productive signal 2).

The γδ T cells of the invention are therefore useful for reducing unwanted 'on target-off tumour' effects. In particular, a normal cell which expresses low levels of a TAA will not activate the γδ T cell of the invention as it will not express a danger signal recognised by the endogenous γδ TCR and thus will not provide signal 1, which is required for full activation of the γδ T cell.

DESCRIPTION OF THE FIGURES

FIG. 10—Nucleic acid and amino acid sequences of an anti-GD2-Fc-DAP10 CAR

FIG. 11—Nucleic acid and amino acid sequences of an anti-CD33-Fc-DAP10 CAR

DETAILED DESCRIPTION

γδ T Cell

T-cells are divided into two groups based on their T-Cell Receptor (TCR) components. The TCR heterodimer consists of an α and β chain in 95% of T cells. These recognise foreign antigens via peptides presented by MHC molecules on antigen presenting cells and are essential for adaptive immunity.

5% of T cells have TCRs consisting of γ and δ chains. γδ TCRs are MHC independent and detect markers of cellular stress expressed by tumours.

γδ T cells recognize pathogens and transformed cells in an HLA-unrestricted manner. They respond to markers of cellular stress (e.g. phosphoantigens released by transformed cells as by-products of the mevalonate biosynthetic pathway). γδ T cells display both innate cytotoxic functions and antigen-presenting capability, particularly in the presence of antibody-opsonized target cells.

γδ T-cells are responsible for "lymphoid stress surveillance," i.e., sensing and responding immediately to infections or non-microbial stress without the need of clonal expansion or de novo differentiation.

The activation of γδ T cells is regulated by a balance between stimulatory and inhibitory signals. They are activated by γδTCR ligands (e.g. phosphoantigens) in combination with MHC-associated ligands of the activatory receptor killer cell lectin-like receptor subfamily K, member 1 (KLRK1), also known as NKG2D, such as MHC class I polypeptide-related sequence A (MICA), MICB, and various members of the UL16-binding protein (ULBP) family.

γδ cells also express killer-cell immunoglobulin-like receptors (KIRs), which can be either activatory or inhibitory, including killer cell immunoglobulin-like receptor, 2 domains, long cytoplasmic tail, 1 (KIR2DL1) and killer cell immunoglobulin-like receptor, 3 domains, long cytoplasmic tail, 1 (KIR3DL1).

Figure 1:
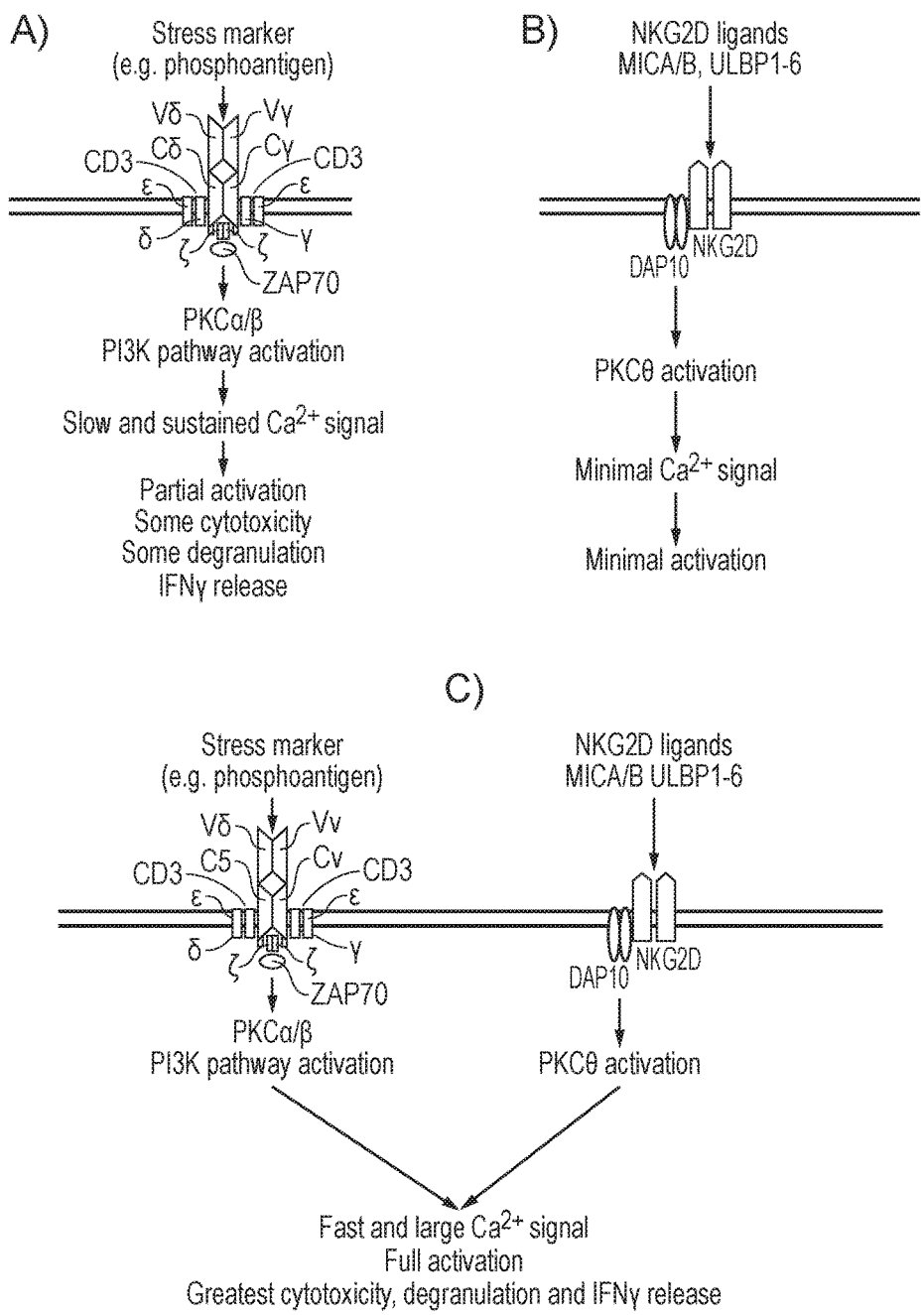
FIG. 1—Diagram of the signalling required for full activation of a γδ T cell which results in killing of the target cell. A) and B) Signalling via the γδ TCR or co-receptors alone does not result in full activation of the γδ T cell. C) A combination of γδ TCR and co-receptor signalling results in full activation of the γδ T cell FIG. 2—Illustrative diagram of a γδ T cell of the present invention. A) Normal activation of a γδ T cell by a target cell. B) Blocking of signal 2 by soluble NKG2D ligands secreted by cancer cells prevents full activation of γδ T cells. C) Full activation of a γδ T cell of the present invention by a transformed cell. D) Normal healthy cells do not express danger signals recognised by endogenous γδ T cell receptors and do not fully activated γδ T cells of the present invention.
Figure 2:
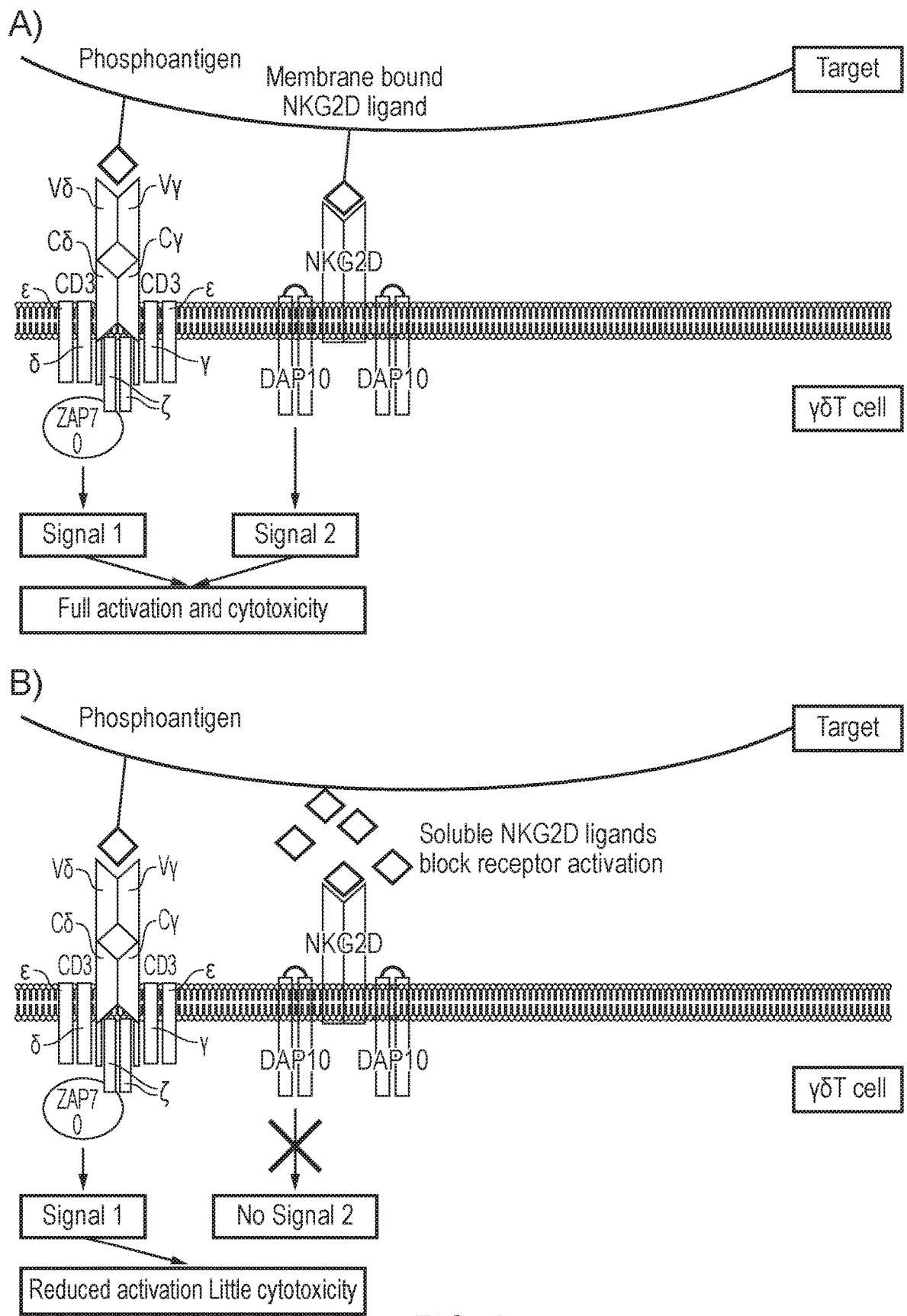
Figure 2:
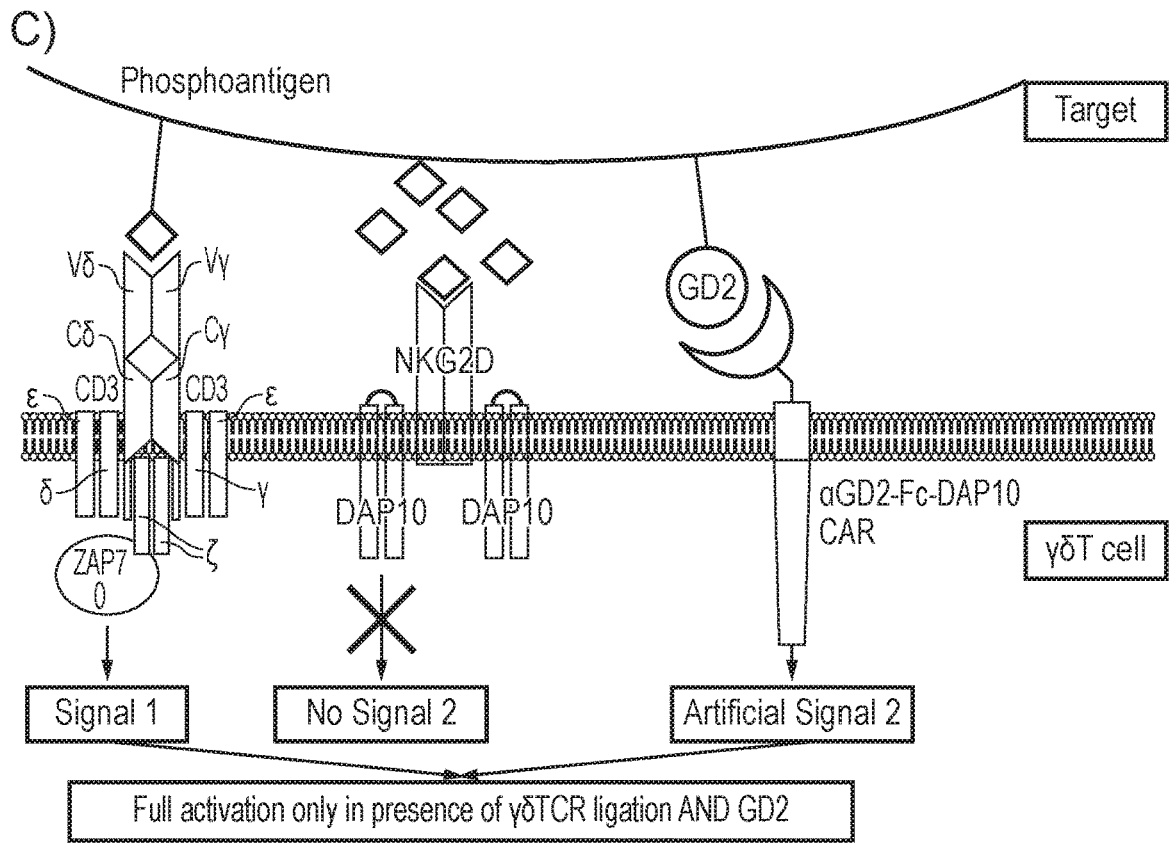
Figure 2:
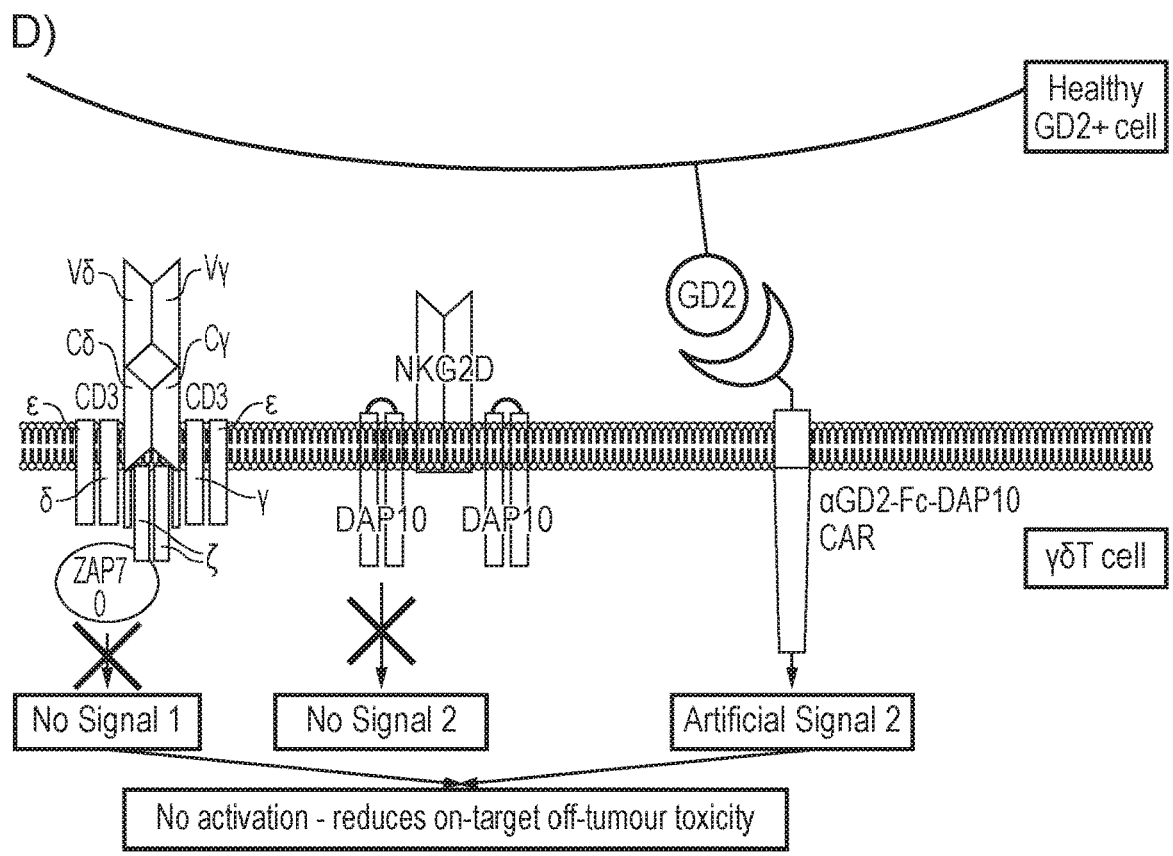
Figure 3:
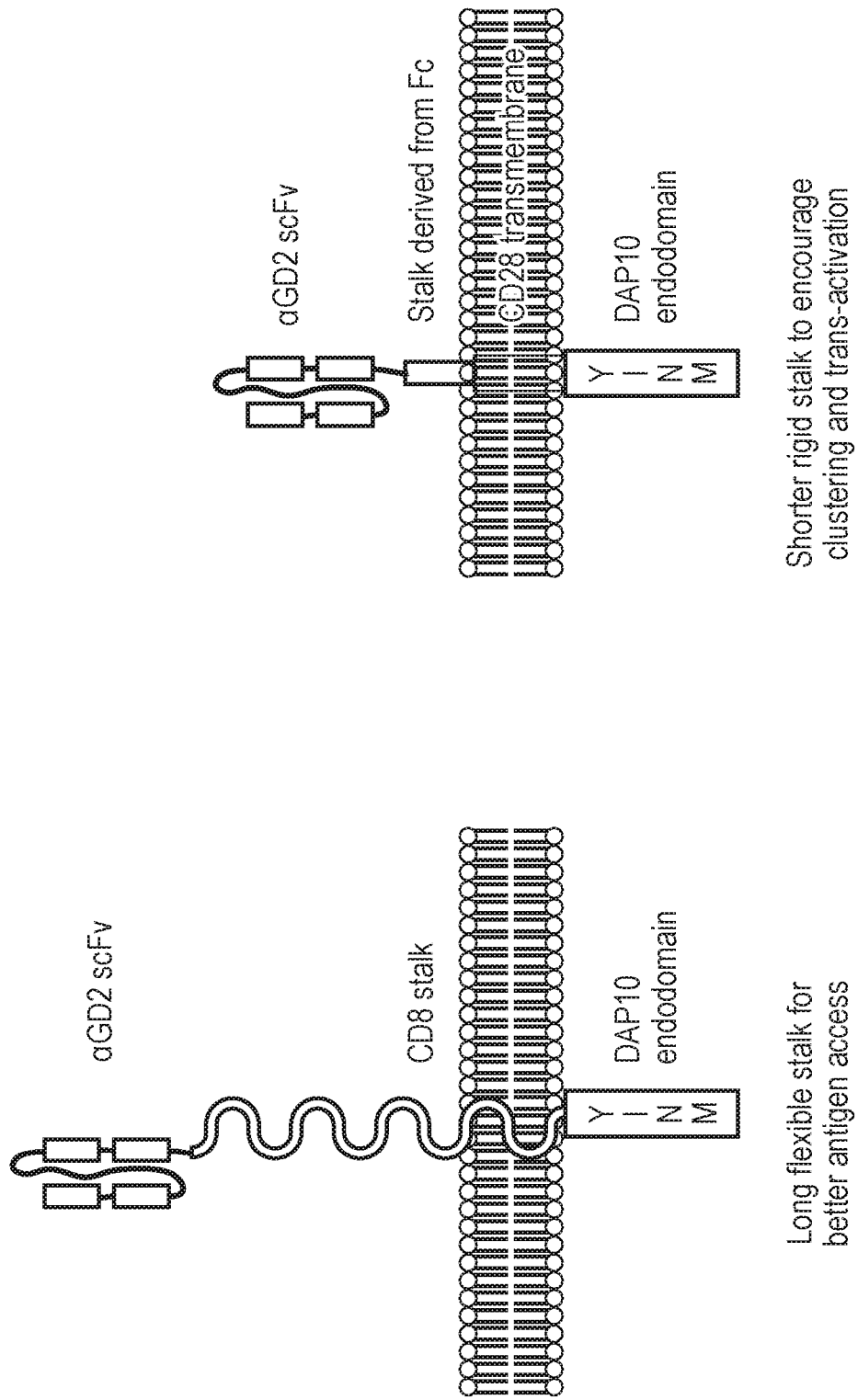
FIG. 3—Examples of illustrative CARs which may be used in the present invention

Full activation of a γδ T cell which results in the effective killing of a target cell requires productive signal 1 and signal 2 generation (FIGS. 1 and 2A).

γδ T-cells derive signal 1 of T cell activation from danger signal antigens present on transformed or infected cells. These danger signal antigens are recognised through the γδ TCR. Signal 2 of T cell activation for γδ T-cells is also commonly derived by danger signal molecules (such as MICA) present on transformed or infected cells. Signal 2 may be transduced, for example, through the NKG2D receptor and DAP 10 (FIG. 2A).

As a means of avoiding immune detection, cancer cells frequently secrete soluble NKG2D ligands effectively blocking signal 2 in γδ T-cells, thus preventing their activation and facilitating tumour infiltration (FIG. 2B).

In a first aspect, the present invention provides a T cell which expresses a γδ TCR and a CAR, wherein the intracellular signalling domain of the CAR provides a co-stimulatory signal to the T cell.

Thus, the arrangement of the γδ TCR and the CAR is such that the γδ TCR provides signal 1 and the CAR provides signal 2 upon binding to each receptor, respectively.

As used herein, co-stimulatory signal is synonymous with signal 2, which is required for full γδ T cell activation.

Thus, a γδ T cell according to the first aspect of the present invention will only be fully activated and capable of killing a target cell which expresses a first antigen which is capable of binding to the γδ TCR (and thus stimulating productive signal 1) and a second antigen which is capable of binding to the CAR (and thus stimulating productive signal 2) (FIG. 2C).

In the absence of antigen binding to the γδ TCR, signal 1 is not generated and full γδ T cell activation is not achieved. In other words, in the absence of antigen binding to the γδ TCR, the γδ T cell is not stimulated to kill the target cell (FIG. 2D).

In the absence of antigen binding to the CAR, signal 2 is not generated and full γδ T cell activation is not achieved. In other words, in the absence of antigen binding to the CAR, the γδ T cell is not stimulated to kill the target cell.

The γδ T cell of the present invention may express any γδ TCR. Examples of γδ TCR ligands are known in the art (see Vantourout, P. & Hayday, A. Nat. Rev. Immunol. 13, 88-100 (2013), for example).

By way of example, the γδ TCR expressed by a cell of the present invention may recognise phosphoantigens (e.g. Isopentenyl pyrophosphate (IPP), Bromohydrin Pyrophosphate (BrHPP) and (E)-4-Hydroxy-3-methyl-but-2-enyl pyrophosphate (HMBPP)); major histocompatibility complex class I chain-related A (MICA); major histocompatibility complex class I chain-related B (MICB); NKG2D ligand 1-6 (ULBP 1-6); CD1c; CD1d; endothelial protein C receptor (EPCR); lipohexapeptides; phycoreythrin or histidyl-tRNA-synthase.

One advantage of the cell of the present invention is that it comprises a CAR comprising (i) an antigen binding domain which binds a specific antigen and (ii) a particular co-stimulatory endodomain. As such, the cell of the present invention will have a greater propensity towards activation in an environment comprising an antigen which can be bound by the CAR, as the binding of antigen by the CAR will result in signalling through the co-stimulatory endodomain and signal 2 production. For example, if the antigen-binding domain of the CAR is specific for a TAA, the cell of the present invention will have an increased propensity towards activation in a tumour environment where the TAA is expressed due to the co-stimulatory signal provided by the CAR.

Chimeric Antigen Receptor

The T cell according to the present invention expresses a chimeric antigen receptor (CAR).

Chimeric antigen receptors (CARs) are engineered receptors which graft an arbitrary specificity onto an immune effector cell. In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to a signaling endodomain. When the CAR binds the target-antigen, this results in the transmission of an activating signal to the T-cell it is expressed on.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

The γδ T cell of the present invention comprises a CAR which comprises a co-stimulatory signalling endodomain which transmits signal 2 to the γδ T cell upon the binding of target antigen.

The CARs of the T cell of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID NO: 6, 7 or 8 or a variant thereof having 5, 4, 3, 2 or 1 amino acid mutations (insertions, substitutions or additions) provided that the signal peptide still functions to cause cell surface expression of the CAR.

```
SEQ ID NO: 6:
MGTSLLCVVMALCLLGADHADG
```

The signal peptide of SEQ ID NO: 6 is compact and highly efficient. It is predicted to give about 95% cleavage after the terminal glycine, giving efficient removal by signal peptidase.

```
SEQ ID NO: 7:
MSLPVTALLLPLALLLHAARP
The signal peptide of SEQ ID NO: 7
is derived from IgG1.

SEQ ID NO: 8:
MAVPTQVLGLLLLWLTDARC
The signal peptide of SEQ ID NO: 8
is derived from CD8.
CO-STIMULATORY INTRACELLULAR
SIGNALLING DOMAIN
```

The intracellular domain/endodomain is the signal-transmission portion of a classical CAR.

The γδ T cell of the present invention comprises a CAR which comprises a co-stimulatory signalling endodomain which transmits signal 2 to the γδ T cell upon the binding of target antigen. Accordingly, γδ T cell of the present invention comprises a CAR which does not transmit signal 1 to the γδ T cell upon the binding of target antigen.

T-cell costimulatory receptors are known to induce qualitative and quantitative changes that lower activation thresholds and prevent T cell anergy and enhance T cell function.

A number of co-receptors for γδ T cells are known in the art. Productive signalling via one or more of these receptors can result in full activation of the γδ T cell and target cell killing.

The γδ T cell of the present invention comprises an intracellular signalling domain from a γδ T cell co-receptor, such that binding of antigen to the antigen-binding domain of the CAR generates productive signal 2 signalling in the γδ T cell.

The intracellular signalling domain may, for example, comprise the DAP10, CD28, CD27, 41 BB, OX40, CD30, IL2-R, IL7-R, IL21-R, NKp30, NKp44 or DNAM-1 (CD226) signalling domain.

The intracellular signalling domain may comprise the DAP10 signalling domain.

DAP10 is a signalling subunit which associates with the NKG2D receptor (see FIG. 1). It is the exclusive binding partner and signalling intermediate for NKG2D and contains a YxxM activation motif that triggers the lipid kinase cascade.

An example of an amino acid sequence for a DAP10 signalling domain is shown below:

```
                                        SEQ ID NO: 3
         CARPRRSPAQEDGKVYINMPGRG
```

Further illustrative co-stimulatory domains are shown as SEQ ID NO: 9-19

```
   (CD28 endodomain)
                                        SEQ ID NO: 9
   KRSRLLHSDYMNMTPRRPGPTRKHYQPYAPPRDFAAY (CD27 endodomain)
                                        SEQ ID NO: 10
   QRRKYRSNKGESPVEPAEPCHYSCPREEEGSTIPIQE

DYRKPEPACSP (41BB endodomain)
                                        SEQ ID NO: 11
   KRGRKKLLYIFKQPFMRPVQTTQEEDGCSCRFPEEEE

GGCEL (OX40 endodomain)
                                        SEQ ID NO: 12
   RRDQRLPPDAHKPPGGGSFRTPIQEEQADAHSTLAKI (CD30 endodomain)
                                        SEQ ID NO: 13
   HRRACRKRIRQKLHLCYPVQTSQPKLELVDSRPRRSS

TQLRSGASVTEPVAEERGLMSQPLMETCHSVGAAYLE

SLPLQDASPAGGPSSPRDLPEPRVSTEHTNNKIEKIY
```

```
                           -continued
   IMKADTVIVGTVKAELPEGRGLAGPAEPELEEELEAD

HTPHYPEQETEPPLGSCSDVMLSVEEEGKEDPLPTAA

SGK (IL2-R endodomain)
                                        SEQ ID NO: 14
   TWQRRQRKSRRTI (IL7-R endodomain)
                                        SEQ ID NO: 15
   KKRIKPIVWPSLPDHKKTLEHLCKKPRKNLNVSFNPE

SFLDCQIHRVDDIQARDEVEGFLQDTFPQQLEESEKQ

RLGGDVQSPNCPSEDWITPESFGRDSSLTCLAGNVSA

CDAPILSSSRSLDCRESGKNGPHVYQDLLLLSLGTTNS

TLPPPFSLQSGILTLNPVAQGQPILTSLGSNQEEAYV

TMSSFYQNQ (IL21-R endodomain)
                                        SEQ ID NO: 16
   SLKTHPLWRLWKKIWAVPSPERFFMPLYKGCSGDFKK

WVGAPFTGSSLELGPWSPEVPSTLEVYSCHPPRSPAK

RLQLTELQEPAELVESDGVPKPSFWPTAQNSGGSAYS

EERDRPYGLVSIDTVTVLDAEGPCTWPCSCEDDGYPA

LDLDAGLEPSPGLEDPLLDAGTTVLSCGCVSAGSPGL

GGPLGSLLDRLKPPLADGEDWAGGLPWGGRSPGGVSE

SEAGSPLAGLDMDTFDSGFVGSDCSSPVECDFTSPGD

EGPPRSYLRQWVVIPPPLSSPGPQAS (NKp30 endodomain)
                                        SEQ ID NO: 17
   GSTVYYQGKCLTWKGPRRQLPAWPAPLPPPCGSSAHL

LPPVPGG (NKp44 endodomain)
                                        SEQ ID NO: 18
   WWGDIWWKTMMELRSLDTQKATCHLQQVTDLPWTSVS

SPVEREILYHTVARTKISDDDDEHTL (DNAM-1 (CD226) endodomain)
                                        SEQ ID NO: 19
   NRRRRRERRDLFTESWDTQKAPNNYRSPISTSQPTNQ

SMDDTREDIYVNYPTFSRRPKTRV
```

The intracellular signalling domain may comprise, consist essentially of or consist of a co-stimulatory signalling domain as described herein.

The intracellular signalling domain may comprise a sequence shown as SEQ ID NO: 3 or 9-19 or a variant thereof.

The variant may comprise a sequence which shares at least 75% sequence identity with SEQ ID NO: 3 or 9-19 provided that the sequence provides an effective co-stimulatory signaling domain.

The variant may comprise a sequence which shares at least 80% sequence identity with SEQ ID NO: 3 or 9-19 provided that the sequence provides an effective co-stimulatory signaling domain.

The variant may comprise a sequence which shares at least 85% sequence identity with SEQ ID NO: 3 or 9-19 provided that the sequence provides an effective co-stimulatory signaling domain.

The variant may comprise a sequence which shares at least 90% sequence identity with SEQ ID NO: 3 or 9-19 provided that the sequence provides an effective co-stimulatory signaling domain.

The variant may comprise a sequence which shares at least 95% sequence identity with SEQ ID NO: 3 or 9-19 provided that the sequence provides an effective co-stimulatory signaling domain.

The variant may comprise a sequence which shares at least 99% sequence identity with SEQ ID NO: 3 or 9-19 provided that the sequence provides an effective co-stimulatory signaling domain.

In one embodiment, the intracellular signalling domain may comprise a sequence shown as SEQ ID NO: 3 or a variant thereof which shares at least 75, 80, 85, 90, 95 or 99% sequence identity with SEQ ID NO: 3, provided that the sequence provides an effective co-stimulatory signaling domain.

In one embodiment, the endodomain does not comprise the CD3 endodomain. For example, the endodomain does not comprise the CD3 epsilon chain, the CD3 gamma chain and/or the CD3 delta chain. In a particular embodiment, the endodomain does not comprise the CD3-zeta endodomain.

An illustrative CD3-zeta endodomain is shown as SEQ ID NO: 26.

```
(CD3 zeta endodomain)
                                    SEQ ID NO: 26
RSRVKFSRSADAPAYQQGQNQLYNELNLGRREEYD

VLDKRRGRDPEMGGKPRRKNPQEGLYNELQKDKMA

EAYSEIGMKGERRRGKGHDGLYQGLSTATKDTYDA

LHMQALPPR
```

The CD3-zeta endodomain as described herein may comprise or consist of SEQ ID NO: 26 or a variant thereof which has at least 80%, 85%, 90%, 95%, 98% or 99% sequence identity to SEQ ID NO: 26 and provides an effective transmembrane domain/intracellular T cell signaling domain.

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell.

By way of example, the examples described herein relate to CARs which bind GD2 and CD33, respectively.

The antigen binding domain may be based on a natural ligand of the antigen.

The antigen binding domain may comprise an affinity peptide from a combinatorial library or a de novo designed affinity protein/peptide.

Tumour-Associated Antigen (TAA)

The antigen binding domain may bind to a tumour-associated antigen (TAA).

An extensive range of TAAs are known in the art and the CAR used in the present invention may comprise any antigen binding domain which is capable of specifically binding to any TAA.

By way of example, the CAR for use in the present invention may be capable of specifically binding to a TAA listed in Table 1.

TABLE 1

| Antigen | Tumour of interest |
|---|---|
| CD20 | B-cell lymphomas, CLL |
| CD19 | Pre-B ALL, B-cell lymphoma, CLL |
| CD22 | Pre-B ALL, B-cell lymphomas, CLL |
| CD30 | Hodgkin's lymphoma, ALCL |
| CD52 | T-cell AML, Pre-B ALL |
| CD70 | Hodgkins Lymphoma, DLCL, Renal cell carcinoma, EBV+ glioblastoma, undifferentiated nasopharyngeal sarcoma |
| CD33 | AML, MDS, APL, CML, JMML, ALL (18% only) |
| CD47 | Pre-B ALL, T cell ALL, AML |
| IL7 receptor α | Pre-B ALL, B cell lymphomas |
| TSLPR | Pre-B ALL (7%), Pre-B aLL in Down's syndrome (60%) |
| ROR1 | Pre-B ALL, CLL mantle cell lymphoma |
| GD2 | Neuroblastoma, osteosarcoma, Ewing sarcoma, soft tissue sarcomas, melanoma |
| IL13Rα2 | Glioblastoma, DIPG, melanoma, various carcinomas, mesothelioma |
| VEGFR2 | Tumour vasculature |
| HER2 | Osteosarcoma, colon cancer, breast cancer |
| ALK | Neuroblastoma, neuroectodermal tumours, glioblastoma, rhabdomyosarcoma, melanoma |
| EGFRvIII | Glioma |
| FGFR4 | Rhabdomyosarcoma |
| B7-H3 | Neuroblastoma |
| Glypican-3/Glypican-5 | Wilm's tumour, neuroblastoma, rhabdomyosarcoma, hepatic carcinaoma, melanoma |
| FOLR1 | Rhabdomyosarcoma, osteosarcoma |

A problem associated with the targeting of TAAs in cancer immunotherapy is that low levels of the TAAs may be expressed on normal tissues. For instance GD2 is a neuroblastoma TAA, but it is also expressed on nerves; PSMA is a prostate cancer TAA but also is found on normal kidney, liver and colon cells, and brain astrocytes. This problem is more profound in solid tumours where there is a dearth of highly selective targets.

The expression of TAAs on normal, healthy cells may result in 'on-target, off-tumour' side effects. The present invention mitigates these effects because the γδ T cell of the present invention is only activated by cells which express a ligand for both the γδ TCR and the CAR. Normal, healthy cells which express the TAA at low levels will therefore not activate the γδ T cell of the present invention because they do not express a danger signal antigen capable of binding to the γδ TCR (FIG. 2D).

The antigen binding domain of the CAR may be capable of binding GD2, CD33, CD19 or EGFR.

Disialoganglioside (GD2, for example as shown by pubchem: 6450346) is a sialic acid-containing glycosphingolipid expressed primarily on the cell surface. The function of this carbohydrate antigen is not completely understood; however, it is thought to play an important role in the attachment of tumour cells to extracellular matrix proteins. GD2 is densely, homogenously and almost universally expressed on neuroblastoma. In normal tissues, GD2 expression is largely limited to skin melanocytes, and peripheral pain fibre myelin sheaths. Within the CNS, GD2 appears to be an embryonic antigen but is found dimly expressed in scattered oligodendrocytes and within the posterior pituitary.

The antigen binding domain may comprise a sequence shown as SEQ ID NO: 20 or a variant thereof, providing that the variant retains the ability to bind to GD2.

```
                                         SEQ ID NO: 20
METDTLLLWVLLLWVPGSTGQVQLQESGPGLVK

PSQTLSITCTVSGFSLASYNIHWVRQPPGKGLEW

LGVIWAGGSTNYNSALMSRLTISKDNSKNQVFLKM

SSLTAADTAVYYCAKRSDDYSWFAYWGQGTLVTVS

SGGGGSGGGGSGGGGSENQMTQSPSSLSASVGDRV

TMTCRASSSVSSSYLHWYQQKSGKAPKVWIYSTSN

LASGVPSRFSGSGSGTDYTLTISSLQPEDFATYYC

QQYSGYPITFGQGTKVEIKRS
```

The antigen binding domain may comprise a sequence shown as SEQ ID NO: 20 or a variant thereof which shares at least 75, 80, 85, 90, 95 or 99% sequence identity with SEQ ID NO: 20, providing that the variant retains the ability to bind to GD2.

CD33 (for example as shown by Uniprot accession number P20138) is a putative adhesion molecule of myelomonocytic-derived cells that mediates sialic-acid dependent binding to cells. It is usually considered myeloid-specific, but it can also be found on some lymphoid cells.

The antigen binding domain may comprise a sequence shown as SEQ ID NO: 21 or a variant thereof, providing that the variant retains the ability to bind to GD2.

```
                                         SEC) ID NO: 21
MAVPTQVLGLLLLWLTDARCDIQMTQSPSSLSASV

GDRVTITCRASEDIYFNLVWYQQKPGKAPKLLIYD

TNRLADGVPSRFSGSGSGTQYTLTISSLQPEDFAT

YYCQHYKNYPLTFGQGTKLEIKRSGGGGSGGGGSG

GGGSGGGGSRSEVQLVESGGGLVQPGGSLRLSCAA

SGFTLSNYGMHWIRQAPGKGLEWVSSISLNGGSTY

YRDSVKGRFTISRDNAKSTLYLQMNSLRAEDTAVY

YCAAQDAYTGGYFDYWGQGTLVTVSSM
```

The antigen binding domain may comprise a sequence shown as SEQ ID NO: 21 or a variant thereof which shares at least 75, 80, 85, 90, 95 or 99% sequence identity with SEQ ID NO: 21, providing that the variant retains the ability to bind to GD2.

The human CD19 antigen is a 95 kd transmembrane glycoprotein belonging to the immunoglobulin superfamily (for example as shown by Uniprot P15391). CD19 is expressed very early in B-cell differentiation and is only lost at terminal B-cell differentiation into plasma cells. Consequently, CD19 is expressed on all B-cell malignancies apart from multiple myeloma. CD19 is also expressed by the normal B cell compartment.

EGFR (for example as shown by Uniprot accession number P00533) is a receptor tyrosine kinase which binds ligands of the EGF family and activates several signaling cascades to convert extracellular cues into appropriate cellular responses. Known ligands include EGF, TGFA/TGF-alpha, amphiregulin, epigen/EPGN, BTC/betacellulin, epiregulin/EREG and HBEGF/heparin-binding EGF. EGFR is expressed at high levels by many cancer cells. However, it is also expressed by normal, healthy cells.

Spacer Domain

CARs may comprise a spacer sequence to connect the antigen-binding domain with the transmembrane domain and spatially separate the antigen-binding domain from the endodomain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
(hinge-CH2CH3 of human IgG1)
                                         SEQ ID NO: 22
AEPKSPDKTHTCPPCPAPPVAGPSVFLFPPKPKDT

LMIARTPEVTCVVVDVSHEDPEVKFNVVYVDGVEV

HNAKTKPREEQYNSTYRVVSVLTVLHQDWLNGKEY

KCKVSNKALPAPIEKTISKAKGQPREPQVYTLPPS

RDELTKNQVSLTCLVKGFYPSDIAVEWESNGQPEN

NYKTTPPVLDSDGSFFLYSKLTVDKSRWQQGNVFS

CSVMHEALHNHYTQKSLSLSPGKKD (human CD8 stalk)
                                         SEQ ID NO: 23
TTTPAPRPPTPAPTIASQPLSLRPEACRPAAGGAV

HTRGLDFACDI (human IgG1 hinge)
                                         SEQ ID NO: 24
AEPKSPDKTHTCPPCPKDPK
```

The spacer may be a variant of any of SEQ ID NO: 22 to 24 which shares at least 70%, at least 75%, at least 80%, at least 85%, at least 90%, at least 95% or at least 99% sequence identity with SEQ ID NO: 22 to 24 and retains the functional activity of the amino acid sequence shown as SEQ ID NO: 9 to 11.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from any type I transmembrane protein. The transmembrane domain may be a synthetic sequence predicted to form a hydrophobic helix.

The transmembrane domain may be derived from CD28, which gives good receptor stability.

The transmembrane domain may comprise the sequence shown as SEQ ID NO: 25.

```
(0D28 transmembrane domain)
                               SEQ ID NO: 25
FWVLVVVGGVLACYSLLVTVAFIIFWV
```

Nucleic Acid

The present invention further provides a nucleic acid sequence which encodes a CAR as described herein.

The nucleic acid sequence may be capable of encoding a CAR having the amino acid sequence shown as SEQ ID NO: 1 or SEQ ID NO: 2.

```
(aCD33-Fc-DAP10 CAR)
                               SEQ ID NO: 4
ATGGCCGTGCCCACTCAGGTCCTGGGGTTGTTGCT

ACTGTGGCTTACAGATGCCAGATGTGACATCCAGA

TGACACAGTCTCCATCTTCCCTGTCTGCATCTGTC

GGAGATCGCGTCACCATCACCTGTCGAGCAAGTGA

GGACATTTATTTTAATTTAGTGTGGTATCAGCAGA

AACCAGGAAAGGCCCCTAAGCTCCTGATCTATGAT

ACAAATCGCTTGGCAGATGGGGTCCCATCACGGTT

CAGTGGCTCTGGATCTGGCACACAGTATACTCTAA

CCATAAGTAGCCTGCAACCCGAAGATTTCGCAACC

TATTATTGTCAACACTATAAGAATTATCCGCTCAC

GTTCGGTCAGGGGACCAAGCTGGAAATCAAAAGAT

CTGGTGGCGGAGGGTCAGGAGGCGGAGGCAGCGGA

GGCGGTGGCTCGGGAGGCGGAGGCTCGAGATCTGA

GGTGCAGTTGGTGGAGTCTGGGGGCGGCTTGGTGC

AGCCTGGAGGGTCCCTGAGGCTCTCCTGTGCAGCC

TCAGGATTCACTCTCAGTAATTATGGCATGCACTG

GATCAGGCAGGCTCCAGGGAAGGGTCTGGAGTGGG

TCTCGTCTATTAGTCTTAATGGTGGTAGCACTTAC

TATCGAGACTCCGTGAAGGGCCGATTCACTATCTC

CAGGGACAATGCAAAAGCACCCTCTACCTTCAAA

TGAATAGTCTGAGGGCCGAGGACACGGCCGTCTAT

TACTGTGCAGCACAGGACGCTTATACGGGAGGTTA

CTTTGATTACTGGGGCCAAGGAACGCTGGTCACAG

TCTCGTCTATGGATCCCGCCGAGCCCAAATCTCCT

GACAAAACTCACACATGCCCACCGTGCCCAGCACC

TCCCGTGGCCGGCCCGTCAGTCTTCCTCTTCCCCC

CAAAACCCAAGGACACCCTCATGATCGCCCGGACC

CCTGAGGTCACATGCGTGGTGGTGGACGTGAGCCA

CGAAGACCCTGAGGTCAAGTTCAACTGGTACGTGG

ACGGCGTGGAGGTGCATAATGCCAAGACAAAGCCG

CGGGAGGAGCAGTACAACAGCACGTACCGTGTGGT

CAGCGTCCTCACCGTCCTGCACCAGGACTGGCTGA

ATGGCAAGGAGTACAAGTGCAAGGTCTCCAACAAA

GCCCTCCCAGCCCCCATCGAGAAAACCATCTCCAA

AGCCAAAGGGCAGCCCCGAGAACCACAGGTGTACA

CCCTGCCCCCATCCCGGGATGAGCTGACCAAGAAC

CAGGTCAGCCTGACCTGCCTGGTCAAAGGCTTCTA

TCCCAGCGACATCGCCGTGGAGTGGGAGAGCAATG

GGCAACCGGAGAACAACTACAAGACCACGCCTCCC

GTGCTGGACTCCGACGGCTCCTTCTTCCTCTACAG

CAAGCTCACCGTGGACAAGAGCAGGTGGCAGCAGG

GGAACGTCTTCTCATGCTCCGTGATGCATGAGGCC

CTGCACAATCACTATACCCAGAAATCTCTGAGTCT

GAGCCCAGGCAAGAAGGACCCCAAGTTCTGGGTCC

TGGTGGTGGTGGGAGGCGTGCTGGCCTGTTACTCT

CTCCTGGTGACCGTGGCCTTCATCATCTTCTGGGT

GTGCGCCAGACCACGGCGGAGCCCAGCCCAGGAGG

ACGGCAAGGTGTACATCAACATGCCCGGCCGCGGC

TGA (aGD2-Fc-DAP10 CAR)
                               SEQ ID NO: 5
ATGGAGACCGACACCCTGCTGCTGTGGGTGCTGCT

GCTGTGGGTGCCAGGCAGCACCGGCCAGGTGCAGC

TGCAGGAGTCTGGCCCAGGCCTGGTGAAGCCCAGC

CAGACCCTGAGCATCACCTGCACCGTGAGCGGCTT

CAGCCTGGCCAGCTACAACATCCACTGGGTGCGGC

AGCCCCCAGGCAAGGGCCTGGAGTGGCTGGGCGTG

ATCTGGGCTGGCGGCAGCACCAACTACAACAGCGC

CCTGATGAGCCGGCTGACCATCAGCAAGGACAACA

GCAAGAACCAGGTGTTCCTGAAGATGAGCAGCCTG

ACAGCCGCCGACACCGCCGTGTACTACTGCGCCAA

GCGGAGCGACGACTACAGCTGGTTCGCCTACTGGG

GCCAGGGCACCCTGGTGACCGTGAGCTCTGGCGGA

GGCGGCTCTGGCGGAGGCGGCTCTGGCGGAGGCGG

CAGCGAGAACCAGATGACCCAGAGCCCCAGCAGCT

TGAGCGCCAGCGTGGGCGACCGGGTGACCATGACC

TGCAGAGCCAGCAGCAGCGTGAGCAGCAGCTACCT
```

-continued

```
GCACTGGTACCAGCAGAAGAGCGGCAAGGCCCCAA

AGGTGTGGATCTACAGCACCAGCAACCTGGCCAGC

GGCGTGCCCAGCCGGTTCAGCGGCAGCGGCAGCGG

CACCGACTACACCCTGACCATCAGCAGCCTGCAGC

CCGAGGACTTCGCCACCTACTACTGCCAGCAGTAC

AGCGGCTACCCCATCACCTTCGGCCAGGGCACCAA

GGTGGAGATCAAGCGGTCGGATCCCGCCGAGCCCA

AATCTCCTGACAAAACTCACACATGCCCACCGTGC

CCAGCACCTCCCGTGGCCGGCCCGTCAGTCTTCCT

CTTCCCCCCAAAACCCAAGGACACCCTCATGATCG

CCCGGACCCCTGAGGTCACATGCGTGGTGGTGGAC

GTGAGCCACGAAGACCCTGAGGTCAAGTTCAACTG

GTACGTGGACGGCGTGGAGGTGCATAATGCCAAGA

CAAAGCCGCGGGAGGAGCAGTACAACAGCACGTAC

CGTGTGGTCAGCGTCCTCACCGTCCTGCACCAGGA

CTGGCTGAATGGCAAGGAGTACAAGTGCAAGGTCT

CCAACAAAGCCCTCCCAGCCCCCATCGAGAAAACC

ATCTCCAAAGCCAAAGGGCAGCCCCGAGAACCACA

GGTGTACACCCTGCCCCCATCCCGGGATGAGCTGA

CCAAGAACCAGGTCAGCCTGACCTGCCTGGTCAAA

GGCTTCTATCCCAGCGACATCGCCGTGGAGTGGGA

GAGCAATGGGCAACCGGAGAACAACTACAAGACCA

CGCCTCCCGTGCTGGACTCCGACGGCTCCTTCTTC

CTCTACAGCAAGCTCACCGTGGACAAGAGCAGGTG

GCAGCAGGGGAACGTCTTCTCATGCTCCGTGATGC

ATGAGGCCCTGCACAATCACTATACCCAGAAATCT

CTGAGTCTGAGCCCAGGCAAGAAGGACCCCAAGTT

CTGGGTCCTGGTGGTGGTGGGAGGCGTGCTGGCCT

GTTACTCTCTCCTGGTGACCGTGGCCTTCATCATC

TTCTGGGTGTGCGCCAGACCACGGCGGAGCCCAGC

CCAGGAGGACGGCAAGGTGTACATCAACATGCCCG

GCCGCGGCTGA
```

The nucleic acid sequence may encode the same amino acid sequence as that encoded by SEQ ID NO: 1 or 2, but may have a different nucleic acid sequence, due to the degeneracy of the genetic code. The nucleic acid sequence may have at least 80, 85, 90, 95, 98 or 99% identity to the sequence shown as SEQ ID NO: 4 or SEQ ID NO: 5, provided that it encodes a CAR as defined in the first aspect of the invention.

Variant

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % sequence identity. The software typically does this as part of the sequence comparison and generates a numerical result.

The terms "variant" according to the present invention includes any substitution of, variation of, modification of, replacement of, deletion of or addition of one (or more) amino acids from or to the sequence providing the resultant amino acid sequence retains substantially the same activity as the unmodified sequence.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

A nucleic acid sequence or amino acid sequence as described herein may comprise, consist of or consist essentially of a nucleic acid sequence or amino acid sequence as shown herein.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector, such as a retroviral vector or a lentiviral vector.

The vector may be capable of transfecting or transducing a T cell.

The vector may also comprise a nucleic acid sequence encoding a suicide gene, such as iCasp9 or RQR8.

A suicide-gene is a genetically encoded mechanism which allows selective destruction of adoptively transferred cells, such as T-cells, in the face of unacceptable toxicity.

Activation of Caspase 9 results in cell apoptosis. The activation mechanism behind Caspase 9 was exploited by the iCasp9 molecule. All that is needed for Caspase 9 to become activated, is overcoming the energic barrier for Caspase 9 to homodimerize. The homodimer undergoes a conformational change and the proteolytic domain of one of a pair of dimers becomes active. Physiologically, this occurs by binding of the CARD domain of Caspase 9 to APAF-1. In iCasp9, the APAF-1 domain is replaced with a modified FKBP12 which has been mutated to selectively bind a chemical inducer of dimerization (CID). Presence of the CID results in homodimerization and activation. iCasp9 is based on a modified human caspase 9 fused to a human FK506 binding protein (FKBP) (Straathof et al (2005) Blood 105:4247-4254). It enables conditional dimerization in the presence of a small molecule CID, known as AP1903.

Expression of RQR8 renders T-cells susceptible to anti-CD20 antibody Rituximab but is more compact than the full-length CD20 molecule (Philip, B. et al. (2014) Blood doi:10.1182/blood-2014-01-545020).

Pharmaceutical Composition

The present invention also relates to a pharmaceutical composition containing a vector or a CAR-expressing T cell of the invention together with a pharmaceutically acceptable carrier, diluent or excipient, and optionally one or more further pharmaceutically active polypeptides and/or compounds. Such a formulation may, for example, be in a form suitable for intravenous infusion.

Method

The present invention also relates to a method for making a cell according to the present invention, which comprises the step of introducing a nucleic acid sequence or vector according to the present invention into a cell.

CAR-expressing cells according to the present invention may either be created ex vivo either from a patient's own peripheral blood (1st party), or in the setting of a haematopoietic stem cell transplant from donor peripheral blood (2nd party), or peripheral blood from an unconnected donor (3rd party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

The method may further comprise stimulating the cell with a γδ T cell stimulating agent. As used herein, a 'γδ T cell stimulating agent' refers to any agent which selectively stimulates the proliferation and/or survival of γδ T cells from a mixed starting population of cells.

Thus, the resulting cell population is enriched with an increased number of γδ T cells—for example particular γδ T cells expressing a particular γδ TCR receptor—compared with the starting population of cells.

γδ T cell populations produced in accordance with the present invention may be enriched with γδ T cells, for example particular γδ T cells expressing a particular γδ TCR receptor. That is, the γδ T cell population that is produced in accordance with the present invention will have an increased number of γδ T cells. For example, the γδ T cell population of the invention will have an increased number of γδ T cells expressing a particular γδ TCR receptor compared with the γδ T cells in a sample isolated from a subject. That is to say, the composition of the γδ T cell population will differ from that of a "native" T cell population (i.e. a population that has not undergone expansion steps discussed herein), in that the percentage or proportion of γδ T cells will be increased.

The γδ T cell population according to the invention may have at least about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100% γδ T cells.

The γδ T cell population according to the invention may have at least about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100% γδ T cells expressing a particular γδ TCR receptor.

By way of example, the γδ T cell stimulating agent may be isopentenyl pyrophosphate (IPP); an analog of IPP (e.g. bromohydrin pyrophosphate or (E)-4-Hydroxy-3-methyl-but-2-enyl pyrophosphate); an inhibitor of farnesyl pyrophosphate synthase (FPPS) or an aminobisphosphonate such as zoledronate or pamidronate.

The γδ T cell stimulating agent may be used in combination with a general T cell mitogen, for example a mitogenic cytokine such as IL-2.

Additional methods of stimulating γδ T cells are known in art and include, for example, the use of Concanavalin A (Siegers, G. M. et al. PLoS ONE 6, e16700 (2011)), anti-γδ TCR antibodies immobilised on plastic; engineered artificial antigen presenting cells as feeders and engineered artificial antigen presenting cells coated in anti-γδ TCR antibody (Fisher, J. et al.; Clin. Cancer Res. (2014)).

Method of Treatment

A method for the treatment of disease relates to the therapeutic use of a vector or T cell of the invention. In this respect, the vector or T cell may be administered to a subject having an existing disease or condition in order to lessen, reduce or improve at least one symptom associated with the disease and/or to slow down, reduce or block the progression of the disease.

CAR-expressing T cells may either be created ex vivo either from a patient's own peripheral blood (1st party), or in the setting of a haematopoietic stem cell transplant from donor peripheral blood (2nd party), or peripheral blood from an unconnected donor (3rd party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

In one embodiment, the sample comprising γδ T cell may have been previously isolated from the subject.

A CAR T cell according to the present invention may be generated by a method as described herein. In particular, a CAR- expressing T cell for use in a method for the treatment of a disease may be generated by a method comprising the steps of transduction of the T cell with a viral vector or transfection with DNA or RNA encoded the co-stimulatory CAR as described herein and expansion of γδ T cells using a γδ T cell stimulating agent.

The γδ T cell stimulating agent may be isopentenyl pyrophosphate (IPP); an analog of IPP (e.g. bromohydrin pyrophosphate or (E)-4-Hydroxy-3-methyl-but-2-enyl pyrophosphate); an inhibitor of farnesyl pyrophosphate synthase (FPPS) or aminobisphosphonates such as zoledronate or pamidronate, for example.

T cells expressing a CAR molecule of the present invention may be used for the treatment of a various diseases including, for example, cancer, microbial infection and viral infection.

The cancer may be, for example, bladder cancer, breast cancer, colon cancer, endometrial cancer, kidney cancer (renal cell), lung cancer, brain cancer, melanoma, leukaemia, lymphoma, pancreatic cancer, prostate cancer or thyroid cancer.

The methods and uses according to the present invention may be practiced in combination with additional compositions. For example, where the disease to be treated is cancer, the composition of the present invention may be administered in combination with additional cancer therapies such as chemotherapy and/or radiotherapy.

A composition of the present invention may be administered in combination with a γδ T cell stimulating agent such as isopentenyl pyrophosphate (IPP); an analog of IPP (e.g. bromohydrin pyrophosphate or (E)-4-Hydroxy-3-methyl-but-2-enyl pyrophosphate); an inhibitor of farnesyl pyrophosphate synthase (FPPS) or aminobisphosphonates such as zoledronate or pamidronate.

In particular, Zoledronate and Pamidronate can be used for in vivo expansion of Vδ2+ γδ T cells in combination with IL-2. There are a number of Phase I clinical trials that have used this approach (see Fisher et al.; OncoImmunology; 3; e27572).

'In combination' may refer to administration of the additional therapy or γδ T cell stimulating agent before, at the same time as or after administration of the composition according to the present invention.

The invention will now be further described by way of Examples, which are meant to serve to assist one of ordinary skill in the art in carrying out the invention and are not intended in any way to limit the scope of the invention.

EXAMPLES

Example 1

Generation of γδ T Cells Expressing a Co-Stimulatory CAR

PBMCs were extracted from the blood of healthy donors using Ficoll density gradient separation. They were cultured in RPMI 1640 medium supplemented with 10% FCS, 1% penicillin/streptomycin, 100 u/ml human IL-2 and 5 µM zoledronic acid for 5 days.

After 5 days they were transduced with retrovirus containing the CAR construct fused to RQR8, which acts as a marker gene and also provides a Rituximab (αCD20) sensitive suicide gene.

The illustrative CAR described herein includes aGD2-specific scFv, a linker based on the Fc portion of IgG1, a transmembrane domain derived from CD28 and the endodomain of DAP10 (see FIG. 10).

A second illustrative CAR includes a CD33-specific scFv, a linker based on the Fc portion of IgG1, a transmembrane domain derived from CD28 and the endodomain of DAP10 (see FIG. 11).

Figure 4:
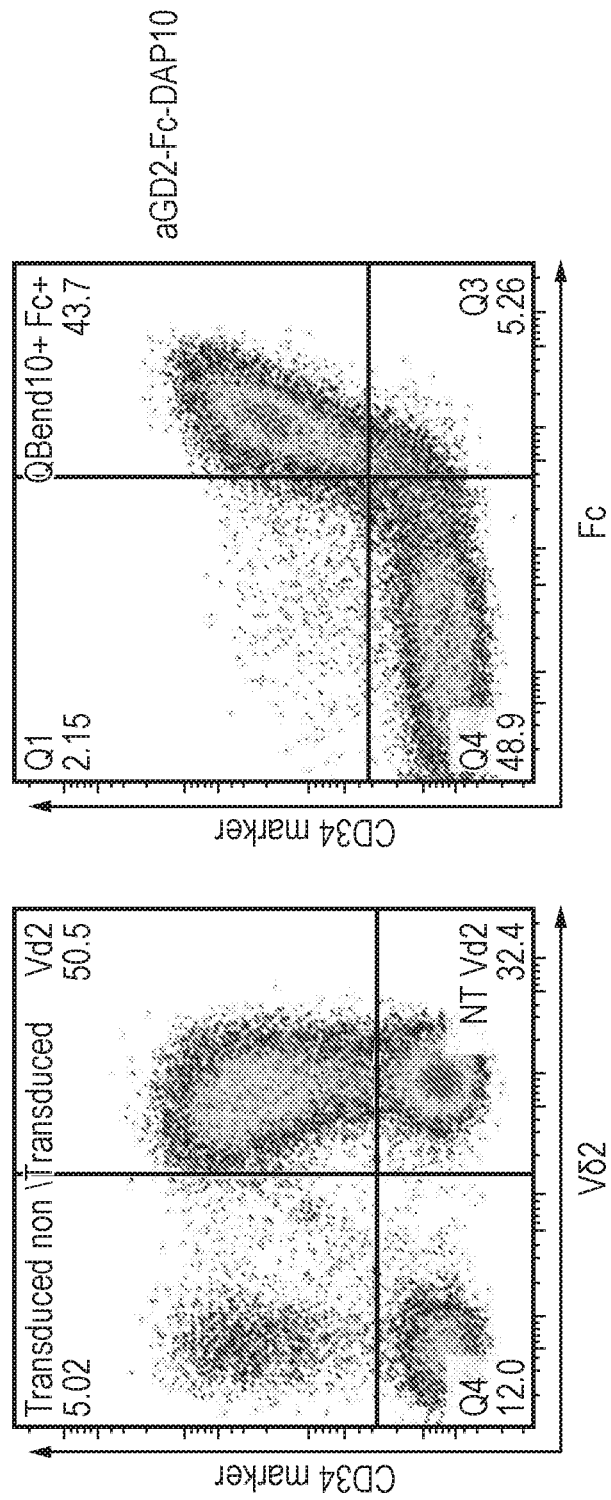
FIG. 4—Representative flow cytometric dot plots to illustrate co-expression of a γδ TCR (Vδ2) and GD2-DAP10 CAR (Fc, CD20 marker and CD34 marker) in a γδ T cell FIG. 5—Killing of GD2+ cell lines LAN1 and TC71 by Vδ2 γδT cells transduced with the aGD2-Fc-DAP10 CAR (A) Significant killing of GD2+ neuroblastoma cell line LAN1 is only seen when CAR transduced cells are used and not when non-transduced (NT) Vδ2 are used as effectors. (B) Additive effect of aGD2-Fc-DAP10 CAR when combined with 24 h zoledronic acid exposure which increases phosphoantigen production, against the GD2+ Ewing sarcoma cell line TC71. (C) Addition of the CAR to αβT cells, which lack the signal 1 provided by the γδTCR in response to cellular stress, has no effect on cytotoxicity, unlike the effect of the CAR in Vδ2+ γδT cells. This indicates that the CAR signal alone is insufficient for T-cell activation. Error bars denote SEM for 3-6 independent donors.

Co-expression of an anti-GD2-Fc-DAP10 CAR with the endogenous TCR of a γδ T cell was demonstrated (FIG. 4).

Example 2

Killing of GD2+ Cell Lines LAN1 and TC71 by Vδ2 γδT Cells Transduced with the aGD2-Fc-DAP10 CAR Both the LAN1 and TC71 cells lines are known to express GD2.

Figure 5:
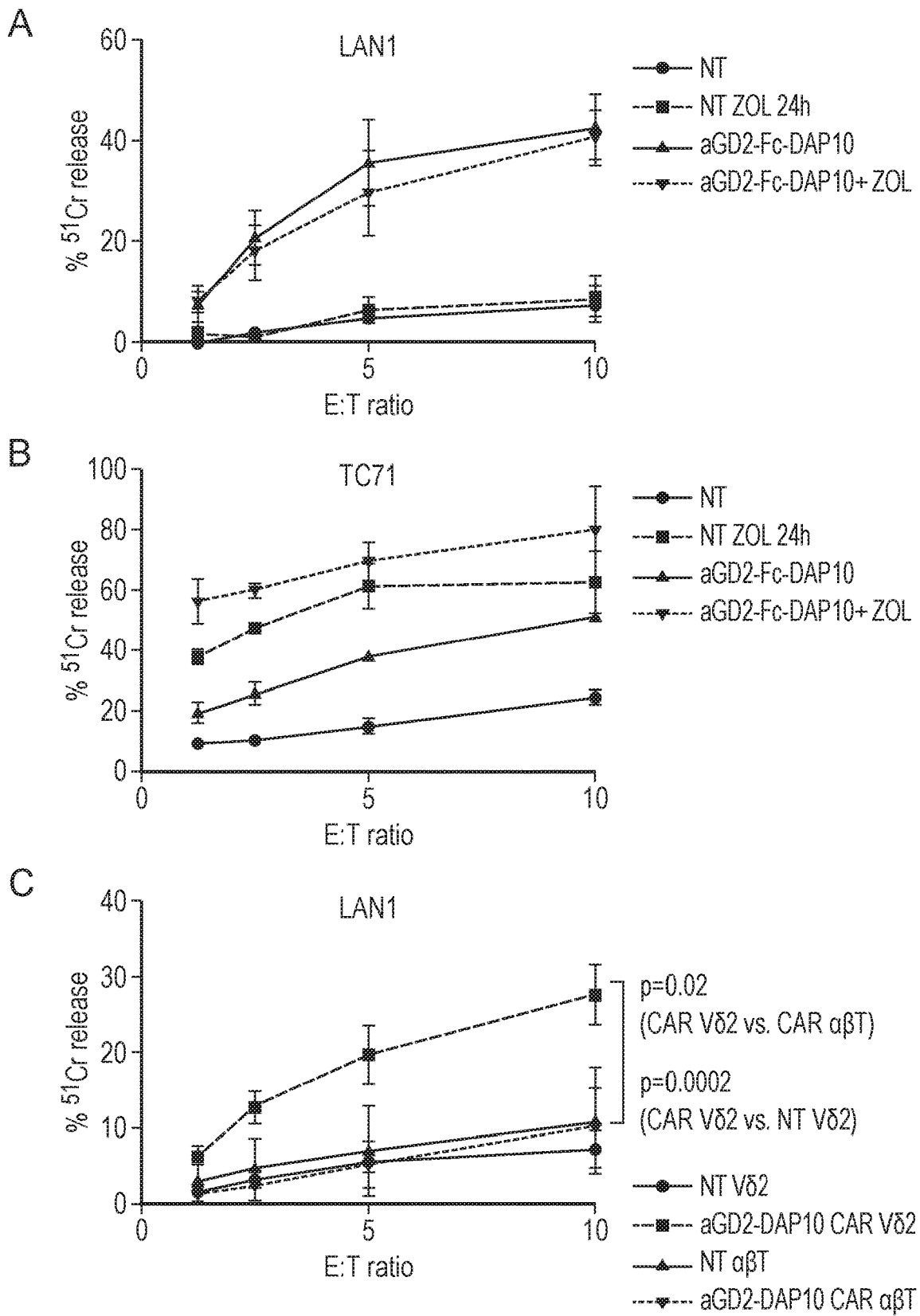

Significant killing of GD2+ neuroblastoma cell line LAN1 was only seen when CAR transduced cells were used and not when non-transduced (NT) Vδ2 cells were used as effectors (FIG. 5A).

There was an additive effect against the GD2+ Ewing sarcoma cell line TC71 when the aGD2-Fc-DAP10 CAR was used in combination with 24 h zoledronic acid treatment (FIG. 5B).

Addition of the CAR to αβT cells, which lack the signal 1 provided by the γδTCR in response to cellular stress, had no effect on cytotoxicity, unlike the effect of the CAR in Vδ2+ γδT cells (FIG. 5C). This indicates that the CAR signal alone is insufficient for T-cell activation.

Figure 6:
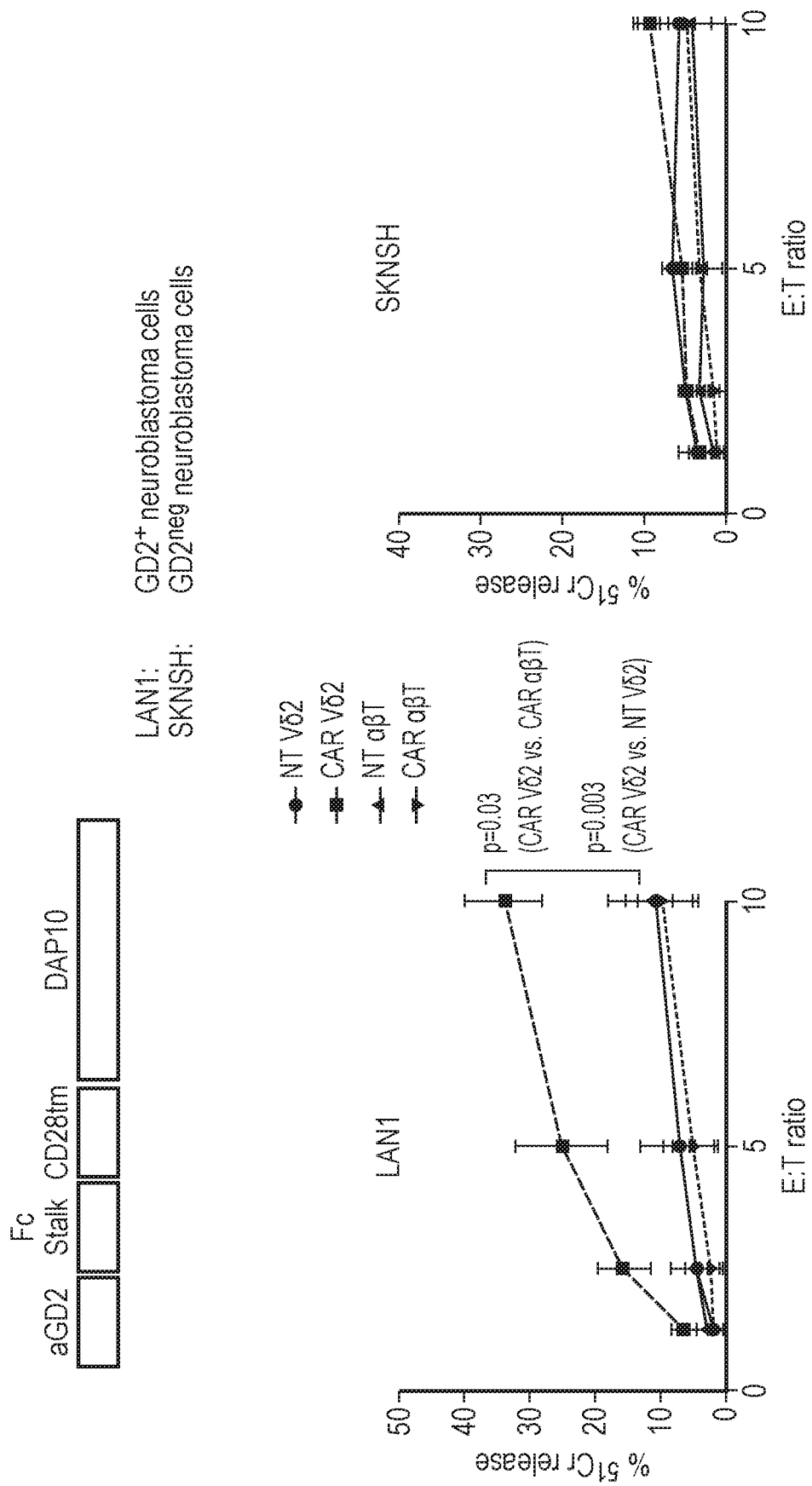
FIG. 6—Killing of GD2+ cell line LAN1 and no killing of GD2− cell line SKNSH. Error bars denote SEM for 3-6 independent donors.

Expression of the aGD2-Fc-DAP10 CAR in γδ T cells did not result in GD2-specific killing of GD2 negative SK-N-SH cells (FIG. 6).

Example 3

Figure 7:
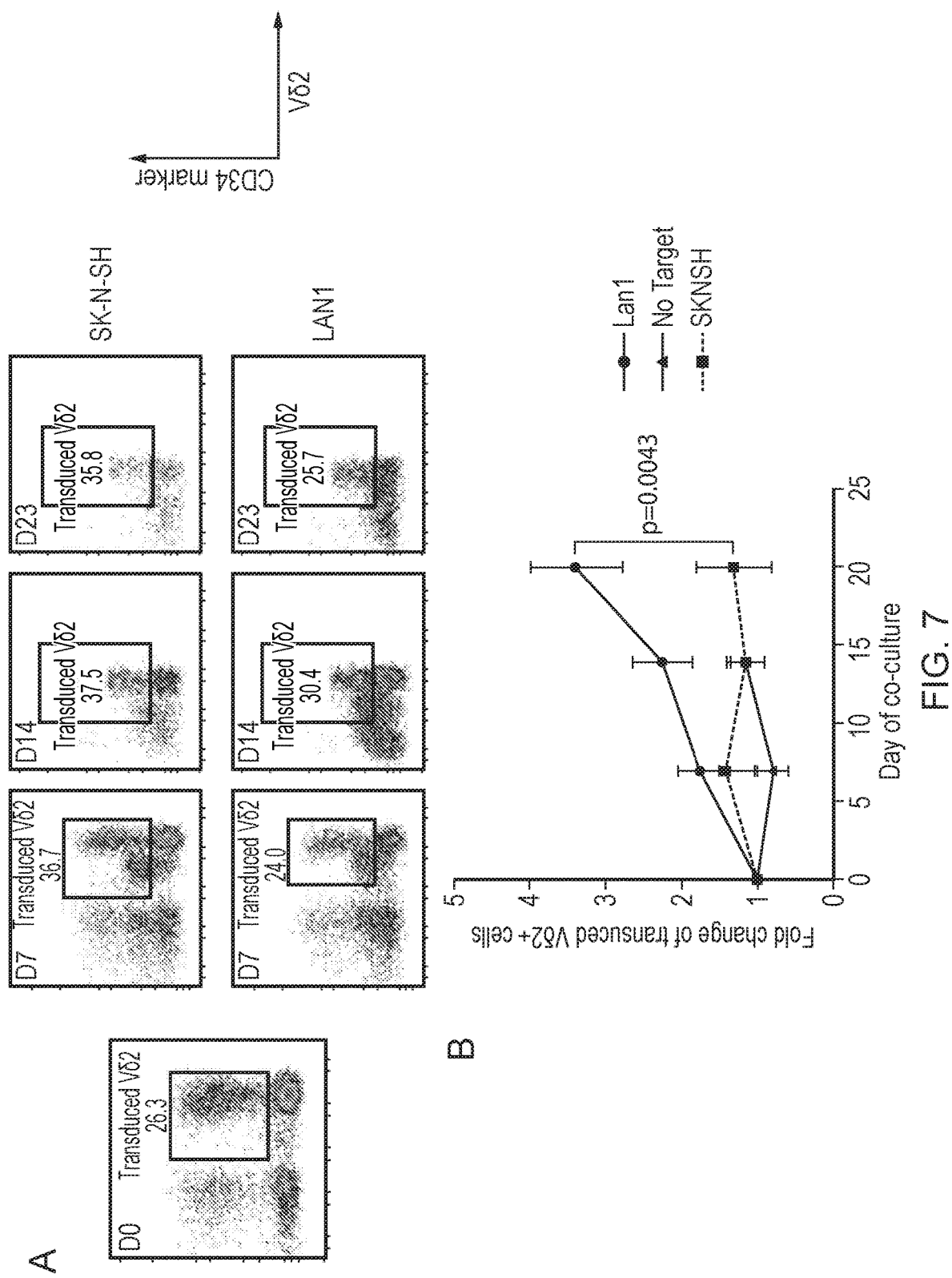
FIG. 7—Preservation of CAR expression following prolonged co-culture and GD2 specific expansion
(A) Co-culture was started 24 days after transduction (labelled D0). Serial analyses of cells for presence of CAR (Y axis) and TCRVδ2 (X axis) were taken in the presence of irradiated GD2+ (LAN1) and GD2− (SK-N-SH) neuroblastoma cells. Representative data from 1 of 3 donors is shown. (B) Expansion of aGD2-Fc-DAP10 transduced Vδ2+ cells was only seen in the presence of irradiated GD2+ target cells (graphical representation, n=3 independent donors, error bars denote SEM).

Preservation of CAR Expression Following Prolonged Co-Culture and GD2 Specific Expansion Co-culture was started 24 days after transduction and serial analyses of cells for the presence of CAR and TCRVδ2 were taken in the presence of irradiated GD2+ (LAN1) and GD2− (SK-N-SH) neuroblastoma cells (FIG. 7A).

The expansion of aGD2-Fc-DAP10 transduced Vδ2+ cells was only seen in the presence of irradiated GD2+ target cells (FIG. 7B).

Example 4

Figure 8:
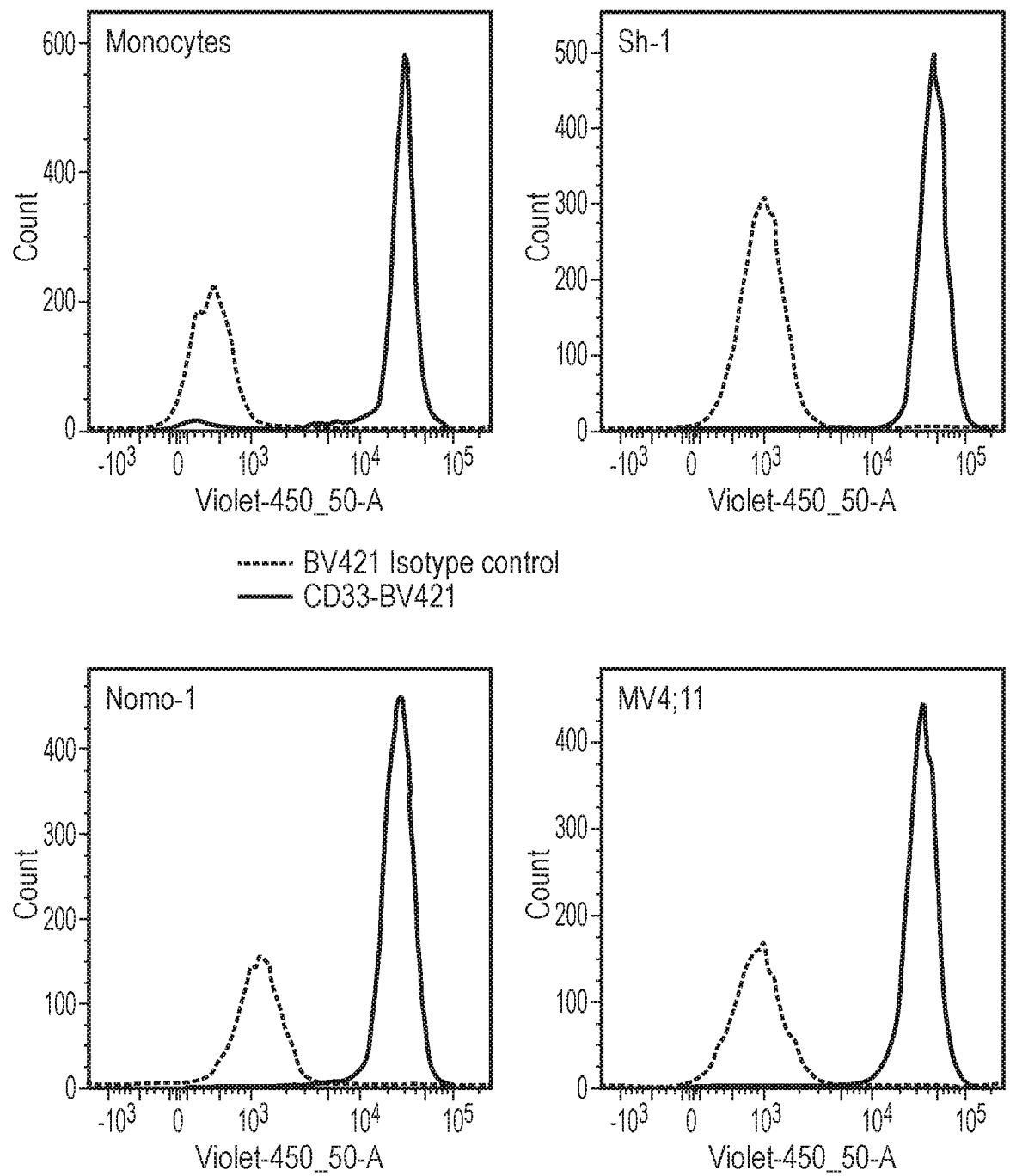
FIG. 8—Flow cytometric staining for CD33 expression of AML cell lines (Nomo1, Sh1 and MV4;11) and freshly isolated monocytes is equivalent.

Specific Killing of CD33+ AML Cells but not CD33+ Monocytes by γδ T Cells Expressing an Anti-CD33-DAP10 CAR Equivalent levels of CD33 expression were demonstrated in three AML cell lines and monocytes (FIG. 8).

Vδ2 γδT cells were transduced with either an anti-CD33-Fc-DAP10 or anti-CD33-Fc-CD28-CD3z CAR construct.

The anti-CD33-Fc-CD28-CD3z CAR construct provides signal 1 and signal 2 in the presence of CD33. The anti-CD33-Fc-DAP10 provides signal 2 in the presence of CD33.

Cells transduced with the aCD33-CD28-CD3z CAR killed any CD33 positive cell and did not spare healthy monocytes. Cells transduced with the aCD33-Fc-DAP10 CAR do not kill monocytes (FIG. 9A).

Figure 9:
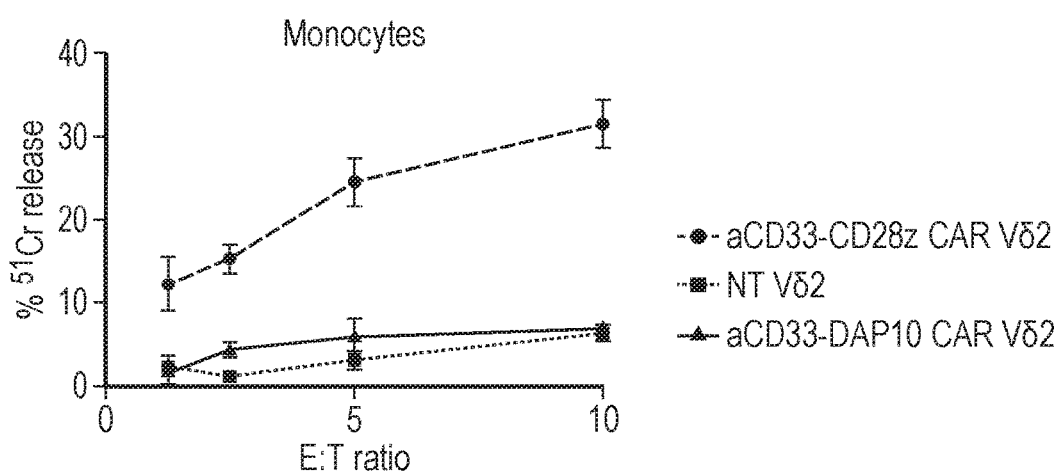
FIG. 9—A) aCD33-DAP10-transduced Vδ2 cells spare monocytes in the absence of ZOL but aCD33-CD28z-transduced Vδ2 cells do not. B) aCD33-DAP10-transduced Vδ2 cells kill AML better than NT Vδ2 cells, but spare monocytes. Error bars indicate SEM for 3 independent donors.
Figure 9:
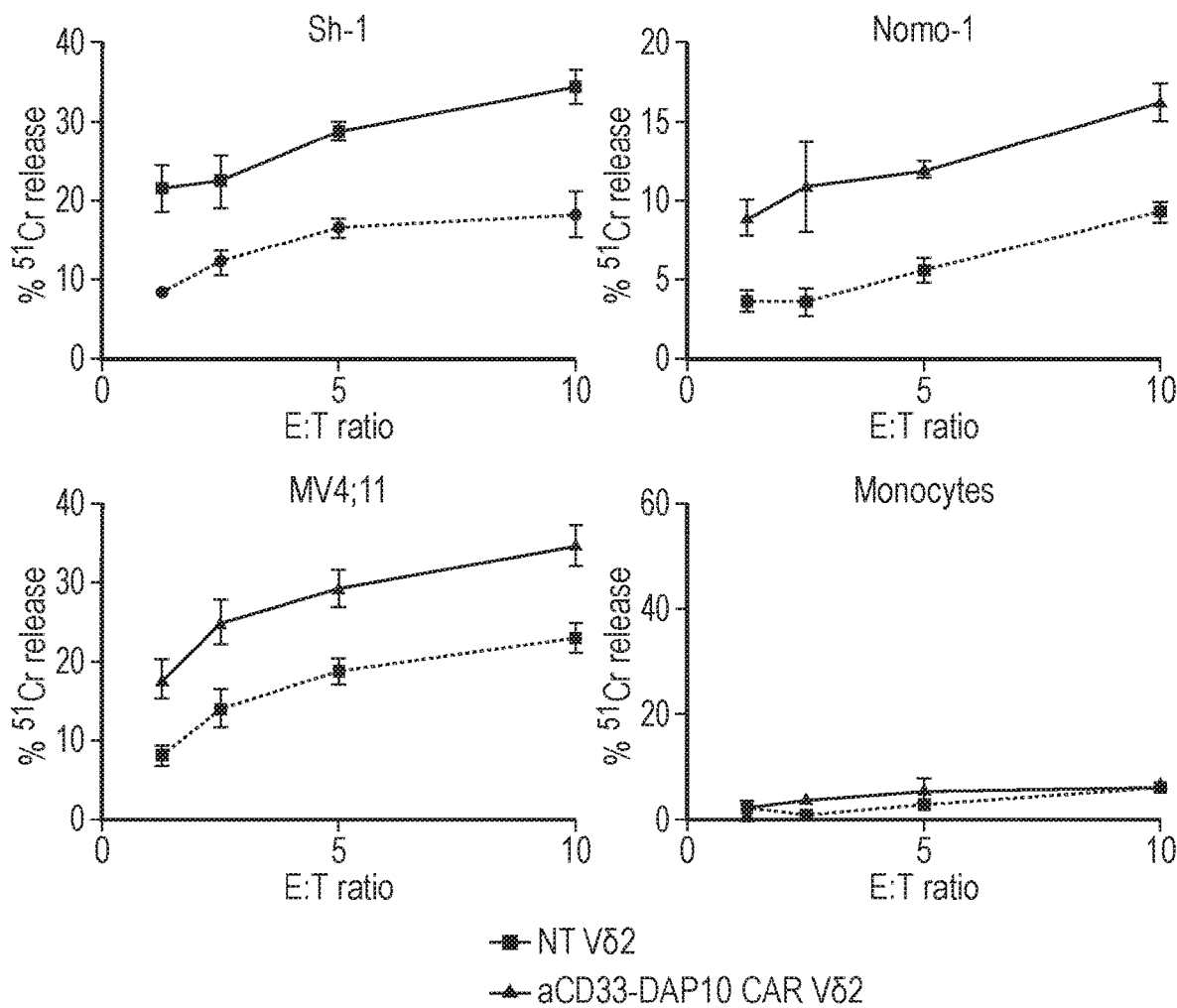
Figure 12:
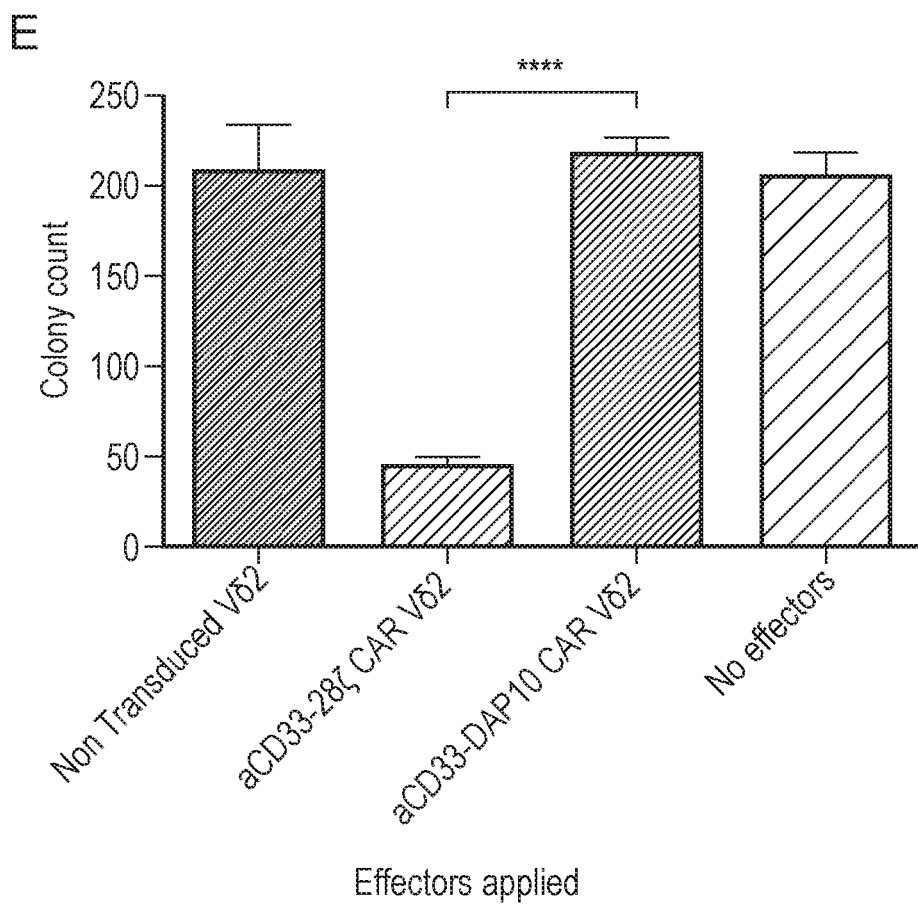
FIG. 12—aCD33-DAP10-transduced Vδ2 cells spare haemopoietic stem cells but aCD33-CD28z-transduced Vδ2 cells do not. Normal human bone marrow was cultured overnight with the indicated CAR T cells. Surviving haemopoietic stem cells were assayed by myeloid colony formation in soft agar. Data is derived using transduced Vδ2 cells from three independent donors.
Figure 13:
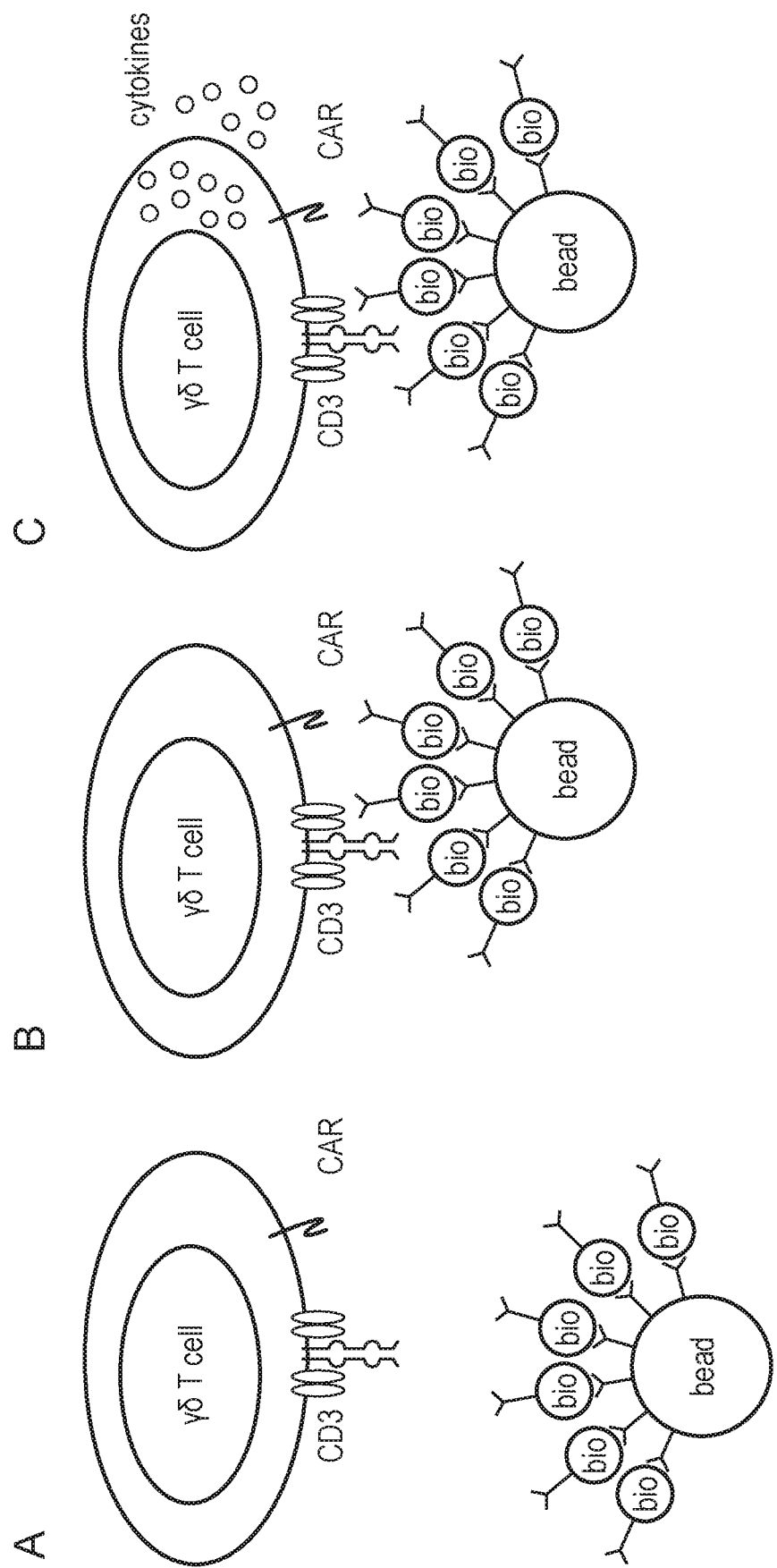
FIG. 13—Differential cross-linking of "costimulation-only" CAR and Vγ9vδ2 TCR leads to differential cytokine responses. Top; Schematic of experimental design. Biotinylated beads are coated with (A) no/irrelevant antibodies, or (B) antibodies to bind either the TCR (anti-CD3) or the CAR (anti-Ig binding the spacer region of the CAR); C) following cross linking, intracellular cytokine secretion is used to measure activation. As a control, stimulatory anti-CD3/CD28 beads (Miltenyi) are used. Bottom-left: representative FACS plots; bottom-right: cytokine responses to cross linking show that the "costimulation-only" CAR cross linking leads to a TNF-α response but that additional TCR engagement is required for full response comprising both interferon gamma and TNF-α. Data is means+/−SD of 5 donors.
Figure 13:
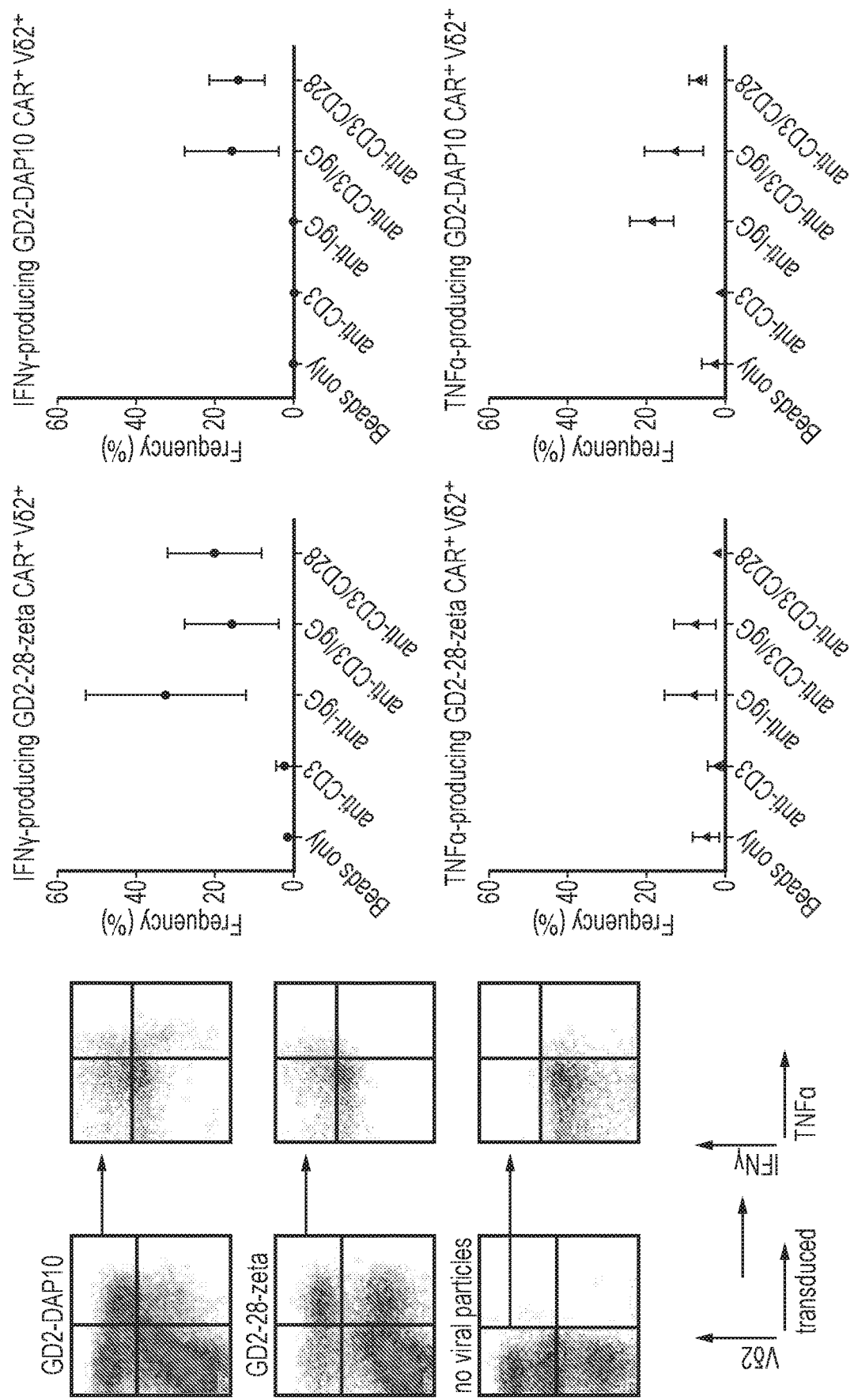

There was significant enhancement of killing of the AML but no enhancement of the killing of monocytes by Vδ2 γδT cells transduced with the aCD33-Fc-DAP10 CAR compared to non-transduced controls (FIG. 9B).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

---

The invention claimed is:

1. A T cell which expresses a gamma-delta T cell receptor (TCR) and a chimeric antigen receptor (CAR), wherein the TCR is used to provide a signal 1 for T cell activation and the CAR is used to provide a co-stimulatory signal 2, and the CAR comprises the amino acid sequence of SEQ ID NO: 2;
   wherein binding of a first antigen to the gamma-delta TCR results in signal 1 production, and
   wherein binding of a second antigen to an antigen-binding domain of the CAR results in a co-stimulatory intracellular signaling domain of the CAR transmitting the co-stimulatory signal 2, but not the signal 1, to the T cell,
   wherein the T cell is activated and capable of killing a target cell which expresses the first antigen capable of binding to the gamma delta TCR and the second antigen capable of binding to the CAR.

2. The cell according to claim 1, wherein the TCR is capable of binding to a phosphoantigen; major histocompatibility complex class I chain-related A (MICA); major histocompatibility complex class I chain-related B (MICB); NKG2D ligand 1-6 (ULBP 1-6); CD1c; CD1d; endothelial protein C receptor (EPCR); lipohexapeptide; phycoreythrin or histidyl-tRNA-synthase.

3. A nucleic acid sequence encoding a CAR as defined in claim 1.

4. A vector comprising a nucleic acid sequence as defined in claim 3.

5. The vector according to claim 4, wherein the vector comprises a retroviral vector, a lentiviral vector, or a transposon.

6. A method for making the cell of claim 1, comprising introducing a nucleic acid sequence encoding the CAR into a T cell expressing a gamma-delta T cell receptor (TCR).

7. The method according to claim 6, wherein the cell is stimulated with a gamma delta T cell stimulating agent.

8. The method according to claim 7, wherein the gamma-delta T cell stimulating agent is selected from isopentenyl pyrophosphate (IPP); analogs of IPP; and inhibitors of farnesyl pyrophosphate synthase (FPPS).

9. The method according to claim 6, wherein the cell is from a sample isolated from a subject.

10. A pharmaceutical composition comprising a cell according to claim 1.

* * * * *

UNITED STATES PATENT AND TRADEMARK OFFICE
CERTIFICATE OF CORRECTION

PATENT NO. : 12,331,316 B2
APPLICATION NO. : 17/528836
DATED : June 17, 2025
INVENTOR(S) : John Anderson et al.

Page 1 of 1

It is certified that error appears in the above-identified patent and that said Letters Patent is hereby corrected as shown below:

In the Claims

In Column 49, Line 41, Claim 2, delete "The cell" and insert -- The T cell --, therefor.

In Column 49, Lines 46-47, Claim 2, delete "phycoreythrin or histidyl-tRNA-synthase" and insert -- phycoerythrin or histidyl-tRNA synthetase --, therefor.

Signed and Sealed this
Ninth Day of December, 2025

John A. Squires
*Director of the United States Patent and Trademark Office*

SEQUENCE LISTING

```
<160> NUMBER OF SEQ ID NOS: 27

<210> SEQ ID NO 1
<211> LENGTH: 560
<212> TYPE: PRT
<213> ORGANISM: Artificial Sequence
<220> FEATURE:
<223> OTHER INFORMATION: aCD33-Fc-DAP10 CAR (chimeric antigen receptor)

<400> SEQUENCE: 1

Met Ala Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asp
        35                  40                  45

Ile Tyr Phe Asn Leu Val Trp Tyr Gln Gln Lys Pro Gly Lys Ala Pro
    50                  55                  60

Lys Leu Leu Ile Tyr Asp Thr Asn Arg Leu Ala Asp Gly Val Pro Ser
65                  70                  75                  80

Arg Phe Ser Gly Ser Gly Ser Gly Thr Gln Tyr Thr Leu Thr Ile Ser
                85                  90                  95

Ser Leu Gln Pro Glu Asp Phe Ala Thr Tyr Tyr Cys Gln His Tyr Lys
            100                 105                 110

Asn Tyr Pro Leu Thr Phe Gly Gln Gly Thr Lys Leu Glu Ile Lys Arg
        115                 120                 125

Ser Gly Gly Gly Gly Ser Gly Gly Gly Gly Ser Gly Gly Gly Gly Ser
    130                 135                 140

Gly Gly Gly Gly Ser Arg Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Thr Leu Ser Asn Tyr Gly Met His Trp Ile Arg Gln Ala Pro
            180                 185                 190

Gly Lys Gly Leu Glu Trp Val Ser Ser Ile Ser Leu Asn Gly Gly Ser
```

```
            195                 200                 205
Thr Tyr Tyr Arg Asp Ser Val Lys Gly Arg Phe Thr Ile Ser Arg Asp
        210                 215                 220

Asn Ala Lys Ser Thr Leu Tyr Leu Gln Met Asn Ser Leu Arg Ala Glu
225                 230                 235                 240

Asp Thr Ala Val Tyr Tyr Cys Ala Ala Gln Asp Ala Tyr Thr Gly Gly
                245                 250                 255

Tyr Phe Asp Tyr Trp Gly Gln Gly Thr Leu Val Thr Val Ser Ser Met
            260                 265                 270

Asp Pro Ala Glu Pro Lys Ser Pro Asp Lys Thr His Thr Cys Pro Pro
        275                 280                 285

Cys Pro Ala Pro Pro Val Ala Gly Pro Ser Val Phe Leu Phe Pro Pro
290                 295                 300

Lys Pro Lys Asp Thr Leu Met Ile Ala Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys Lys Asp Pro Lys Phe Trp
            500                 505                 510

Val Leu Val Val Val Gly Gly Val Leu Ala Cys Tyr Ser Leu Leu Val
        515                 520                 525

Thr Val Ala Phe Ile Ile Phe Trp Val Cys Ala Arg Pro Arg Arg Ser
        530                 535                 540

Pro Ala Gln Glu Asp Gly Lys Val Tyr Ile Asn Met Pro Gly Arg Gly
545                 550                 555                 560

<210> SEQ ID NO 2
<211> LENGTH: 551
<212> TYPE: PRT
<213> ORGANISM: Artificial Sequence
<220> FEATURE:
<223> OTHER INFORMATION: aGD2-Fc-DAP10 CAR

<400> SEQUENCE: 2

Met Glu Thr Asp Thr Leu Leu Leu Trp Val Leu Leu Leu Trp Val Pro
```

```
1               5                   10                  15
Gly Ser Thr Gly Gln Val Gln Leu Gln Glu Ser Gly Pro Gly Leu Val
            20                  25                  30
Lys Pro Ser Gln Thr Leu Ser Ile Thr Cys Thr Val Ser Gly Phe Ser
            35                  40                  45
Leu Ala Ser Tyr Asn Ile His Trp Val Arg Gln Pro Pro Gly Lys Gly
            50                  55                  60
Leu Glu Trp Leu Gly Val Ile Trp Ala Gly Gly Ser Thr Asn Tyr Asn
65                  70                  75                  80
Ser Ala Leu Met Ser Arg Leu Thr Ile Ser Lys Asp Asn Ser Lys Asn
                85                  90                  95
Gln Val Phe Leu Lys Met Ser Ser Leu Thr Ala Ala Asp Thr Ala Val
                100                 105                 110
Tyr Tyr Cys Ala Lys Arg Ser Asp Asp Tyr Ser Trp Phe Ala Tyr Trp
                115                 120                 125
Gly Gln Gly Thr Leu Val Thr Val Ser Ser Gly Gly Gly Gly Ser Gly
            130                 135                 140
Gly Gly Gly Ser Gly Gly Gly Ser Glu Asn Gln Met Thr Gln Ser
145                 150                 155                 160
Pro Ser Ser Leu Ser Ala Ser Val Gly Asp Arg Val Thr Met Thr Cys
                165                 170                 175
Arg Ala Ser Ser Ser Val Ser Ser Ser Tyr Leu His Trp Tyr Gln Gln
                180                 185                 190
Lys Ser Gly Lys Ala Pro Lys Val Trp Ile Tyr Ser Thr Ser Asn Leu
                195                 200                 205
Ala Ser Gly Val Pro Ser Arg Phe Ser Gly Ser Gly Ser Gly Thr Asp
            210                 215                 220
Tyr Thr Leu Thr Ile Ser Ser Leu Gln Pro Glu Asp Phe Ala Thr Tyr
225                 230                 235                 240
Tyr Cys Gln Gln Tyr Ser Gly Tyr Pro Ile Thr Phe Gly Gln Gly Thr
                245                 250                 255
Lys Val Glu Ile Lys Arg Ser Asp Pro Ala Glu Pro Lys Ser Pro Asp
            260                 265                 270
Lys Thr His Thr Cys Pro Pro Cys Pro Ala Pro Val Ala Gly Pro
                275                 280                 285
Ser Val Phe Leu Phe Pro Pro Lys Pro Lys Asp Thr Leu Met Ile Ala
            290                 295                 300
Arg Thr Pro Glu Val Thr Cys Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
                340                 345                 350
Val Ser Val Leu Thr Val Leu His Gln Asp Trp Leu Asn Gly Lys Glu
                355                 360                 365
Tyr Lys Cys Lys Val Ser Asn Lys Ala Leu Pro Ala Pro Ile Glu Lys
                370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
```

```
Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
            500                 505                 510

Ala Cys Tyr Ser Leu Leu Val Thr Val Ala Phe Ile Ile Phe Trp Val
        515                 520                 525

Cys Ala Arg Pro Arg Arg Ser Pro Ala Gln Glu Asp Gly Lys Val Tyr
        530                 535                 540

Ile Asn Met Pro Gly Arg Gly
545                 550

<210> SEQ ID NO 3
<211> LENGTH: 23
<212> TYPE: PRT
<213> ORGANISM: Artificial Sequence
<220> FEATURE:
<223> OTHER INFORMATION: DAP10 signalling domain

<400> SEQUENCE: 3

Cys Ala Arg Pro Arg Arg Ser Pro Ala Gln Glu Asp Gly Lys Val Tyr
1               5                   10                  15

Ile Asn Met Pro Gly Arg Gly
            20

<210> SEQ ID NO 4
<211> LENGTH: 1683
<212> TYPE: DNA
<213> ORGANISM: Artificial Sequence
<220> FEATURE:
<223> OTHER INFORMATION: nucleic acid sequence which encodes a CAR,
      aCD33-Fc-DAP10 CAR

<400> SEQUENCE: 4
atggccgtgc ccactcaggt cctggggttg ttgctactgt ggcttacaga tgccagatgt      60
gacatccaga tgacacagtc tccatcttcc ctgtctgcat ctgtcggaga tcgcgtcacc     120
atcacctgtc gagcaagtga ggacatttat tttaatttag tgtggtatca gcagaaacca     180
ggaaaggccc ctaagctcct gatctatgat acaaatcgct ggcagatggg gtcccatca     240 cggttcagtg ctctggatc tggcacacag tatactctaa ccataagtag cctgcaaccc     300
gaagatttcg caacctatta ttgtcaacac tataagaatt atccgctcac gttcggtcag     360
gggaccaagc tggaaatcaa agatctggt ggcggagggt caggaggcgg aggcagcgga     420
ggcggtggct cgggaggcgg aggctcgaga tctgaggtgc agttggtgga gtctgggggc     480
ggcttggtgc agcctggagg gtccctgagg ctctcctgtg cagcctcagg attcactctc     540
agtaattatg gcatgcactg gatcaggcag gctccaggga aggtctggag gtgggtctcg     600
tctattagtc ttaatggtgg tagcacttac tatcgagact ccgtgaaggg ccgattcact     660
atctccaggg acaatgcaaa aagcaccctc taccttcaaa tgaatagtct gagggccgag     720
gacacggccg tctattactg tgcagcacag gacgcttata cggaggtta ctttgattac     780 tggggccaag gaacgctggt cacagtctcg tctatggatc ccgccgagcc caaatctcct     840
```

```
gacaaaactc acacatgccc accgtgccca gcacctcccg tggccggccc gtcagtcttc    900
ctcttccccc caaaacccaa ggacaccctc atgatcgccc ggaccctga ggtcacatgc     960 gtggtggtgg acgtgagcca cgaagaccct gaggtcaagt tcaactggta cgtggacggc   1020
gtggaggtgc ataatgccaa gacaaagccg cggggaggag agtacaacag cacgtaccgt   1080
gtggtcagcg tcctcaccgt cctgcaccag gactggctga atggcaagga gtacaagtgc   1140
aaggtctcca acaaagccct cccagccccc atcgagaaaa ccatctccaa agccaaaggg   1200
cagccccgag aaccacaggt gtacaccctg cccccatccc gggatgagct gaccaagaac   1260
caggtcagcc tgacctgcct ggtcaaaggc ttctatccca gcgacatcgc cgtggagtgg   1320
gagagcaatg ggcaaccgga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggcc ctgcacaatc actatccca gaaatctctg    1500 agtctgagcc caggcaagaa ggaccccaag ttctgggtcc tggtggtggt gggaggcgtg   1560
ctggcctgtt actctctcct ggtgaccgtg gccttcatca tcttctgggt gtgcgccaga   1620
ccacggcgga gcccagccca ggaggacggc aaggtgtaca tcaacatgcc cggccgcggc   1680
tga                                                                 1683

<210> SEQ ID NO 5
<211> LENGTH: 1656
<212> TYPE: DNA
<213> ORGANISM: Artificial Sequence
<220> FEATURE:
<223> OTHER INFORMATION: nucleic acid sequence which encodes a CAR,
      aGD2-Fc-DAP10 CAR

<400> SEQUENCE: 5
atggagaccg acaccctgct gctgtggtg ctgctgctgt gggtgccagg cagcaccggc     60
caggtgcagc tgcaggagtc tgggcccagg ctggtgaagc ccagcagac cctgagcatc    120 acctgcaccg tgagcggctt cagcctggcc agctacaaca tccactgggt gcggcagccc    180
ccaggcaagg gcctggagtg gctgggcgtg atctgggctg cggcagcac caactacaac    240 agcgccctga tgagccggct gaccatcagc aaggacaaca gcaagaacca ggtgttcctg    300
aagatgagca gcctgacagc cgccgacacc gccgtgtact actgcgccaa gcggagcgac    360
gactacagct ggttcgccta ctggggccag ggcaccctgg tgaccgtgag ctctggcgga    420
ggcggctctg gcggaggcgg ctctggcgga ggcggcagcg agaaccagat gacccagagc    480
cccagcagct tgagcgccag cgtgggcgac cgggtgacca tgacctgcag agccagcagc    540
agcgtgagca gcagctacct gcactggtac cagcagaaga gcggcaaggc ccccaaaggtg   600 tggatctaca gcaccagcaa cctggccagc ggcgtgccca gccggttcag cggcagcggc   660
agcggcaccg actacaccct gaccatcagc agcctgcagc cgaggacttt cgccacctac   720
tactgccagc agtacagcgg ctacccatc accttcggcc agggcaccaa ggtggagatc   780
aagcggtcgg atcccgccga gcccaaatct cctgacaaaa ctcacacatg cccaccgtgc   840
ccagcacctc ccgtggccgg cccgtcagtc ttcctcttcc ccccaaaacc caaggacacc   900
ctcatgatcg cccggacccc tgaggtcaca tgcgtggtgg tggacgtgag ccacgaagac   960
cctgaggtca agttcaactg gtacgtggac ggcgtggagg tgcataatgc caagacaaag   1020
ccgcgggagg agcagtacaa cagcacgtac cgtgtggtca gcgtcctcac cgtcctgcac   1080
caggactggc tgaatggcaa ggagtacaag tgcaaggtct ccaacaaagc cctcccagcc   1140
```

```
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc ccagcgacat cgccgtggag tgggagagca atgggcaacc ggagaacaac    1320
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gccctgcaca atcactatac ccagaaatct ctgagtctga gcccaggcaa gaaggacccc    1500
aagttctggg tcctggtggt ggtgggaggc gtgctggcct gttactctct cctggtgacc    1560
gtggccttca tcatcttctg ggtgtgcgcc agaccacggc ggagcccagc ccaggaggac    1620
ggcaaggtgt acatcaacat gcccggccgc ggctga                              1656
```

```
<210> SEQ ID NO 6
<211> LENGTH: 21
<212> TYPE: PRT
<213> ORGANISM: Artificial Sequence
<220> FEATURE:
<223> OTHER INFORMATION: signal peptide

<400> SEQUENCE: 6

Met Gly Thr Ser Leu Leu Cys Trp Met Ala Leu Cys Leu Leu Gly Ala
1               5                   10                  15

Asp His Ala Asp Gly
            20

<210> SEQ ID NO 7
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 7

Met Ser Leu Pro Val Thr Ala Leu Leu Leu Pro Leu Ala Leu Leu Leu
1               5                   10                  15

His Ala Ala Arg Pro
            20

<210> SEQ ID NO 8
<211> LENGTH: 20
<212> TYPE: PRT
<213> ORGANISM: Artificial Sequence
<220> FEATURE:
<223> OTHER INFORMATION: signal peptide derived from CD8

<400> SEQUENCE: 8

Met Ala Val Pro Thr Gln Val Leu Gly Leu Leu Leu Leu Trp Leu Thr
1               5                   10                  15

Asp Ala Arg Cys
            20

<210> SEQ ID NO 9
<211> LENGTH: 37
<212> TYPE: PRT
<213> ORGANISM: Artificial Sequence
<220> FEATURE:
<223> OTHER INFORMATION: co-stimulatory domain, CD28 endodomain

<400> SEQUENCE: 9

Lys Arg Ser Arg Leu Leu His Ser Asp Tyr Met Asn Met Thr Pro Arg
1               5                   10                  15
```

Arg Pro Gly Pro Thr Arg Lys His Tyr Gln Pro Tyr Ala Pro Pro Arg
            20                  25                  30

Asp Phe Ala Ala Tyr
        35

<210> SEQ ID NO 10
<211> LENGTH: 48
<212> TYPE: PRT
<213> ORGANISM: Artificial Sequence
<220> FEATURE:
<223> OTHER INFORMATION: co-stimulatory domain, CD27 endodomain

<400> SEQUENCE: 10

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 11
<211> LENGTH: 42
<212> TYPE: PRT
<213> ORGANISM: Artificial Sequence
<220> FEATURE:
<223> OTHER INFORMATION: co-stimulatory domain, 41BB endodomain

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 12
<211> LENGTH: 37
<212> TYPE: PRT
<213> ORGANISM: Artificial Sequence
<220> FEATURE:
<223> OTHER INFORMATION: co-stimulatory domain, OX40 endodomain

<400> SEQUENCE: 12

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 13
<211> LENGTH: 188
<212> TYPE: PRT
<213> ORGANISM: Artificial Sequence
<220> FEATURE:
<223> OTHER INFORMATION: co-stimulatory domain, CD30 endodomain

<400> SEQUENCE: 13

His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

Pro Arg Arg Ser Ser Thr Gln Leu Arg Ser Gly Ala Ser Val Thr Glu
        35                  40                  45

Pro Val Ala Glu Glu Arg Gly Leu Met Ser Gln Pro Leu Met Glu Thr
 50                  55                  60

Cys His Ser Val Gly Ala Ala Tyr Leu Glu Ser Leu Pro Leu Gln Asp
 65                  70                  75                  80

Ala Ser Pro Ala Gly Gly Pro Ser Ser Pro Arg Asp Leu Pro Glu Pro
                 85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
            115                 120                 125

Glu Gly Arg Gly Leu Ala Gly Pro Ala Glu Pro Glu Leu Glu Glu Glu
        130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185

<210> SEQ ID NO 14
<211> LENGTH: 13
<212> TYPE: PRT
<213> ORGANISM: Artificial Sequence
<220> FEATURE:
<223> OTHER INFORMATION: co-stimulatory domain, IL2-R endodomain

<400> SEQUENCE: 14

Thr Trp Gln Arg Arg Gln Arg Lys Ser Arg Arg Thr Ile
1               5                   10

<210> SEQ ID NO 15
<211> LENGTH: 195
<212> TYPE: PRT
<213> ORGANISM: Artificial Sequence
<220> FEATURE:
<223> OTHER INFORMATION: co-stimulatory domain, IL7-R endodomain

<400> SEQUENCE: 15

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
 50                  55                  60

Pro Gln Gln Leu Glu Glu Ser Glu Lys Gln Arg Leu Gly Gly Asp Val
 65                  70                  75                  80

Gln Ser Pro Asn Cys Pro Ser Glu Asp Val Val Ile Thr Pro Glu Ser
                 85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
            115                 120                 125

Ser Gly Lys Asn Gly Pro His Val Tyr Gln Asp Leu Leu Leu Ser Leu

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 16
<211> LENGTH: 285
<212> TYPE: PRT
<213> ORGANISM: Artificial Sequence
<220> FEATURE:
<223> OTHER INFORMATION: co-stimulatory domain, IL21-R endodomain

<400> SEQUENCE: 16

Ser Leu Lys Thr His Pro Leu Trp Arg Leu Trp Lys Lys Ile Trp Ala
1               5                   10                  15

Val Pro Ser Pro Glu Arg Phe Phe Met Pro Leu Tyr Lys Gly Cys Ser
            20                  25                  30

Gly Asp Phe Lys Lys Trp Val Gly Ala Pro Phe Thr Gly Ser Ser Leu
        35                  40                  45

Glu Leu Gly Pro Trp Ser Pro Glu Val Pro Ser Thr Leu Glu Val Tyr
    50                  55                  60

Ser Cys His Pro Pro Arg Ser Pro Ala Lys Arg Leu Gln Leu Thr Glu
65                  70                  75                  80

Leu Gln Glu Pro Ala Glu Leu Val Glu Ser Asp Gly Val Pro Lys Pro
                85                  90                  95

Ser Phe Trp Pro Thr Ala Gln Asn Ser Gly Gly Ser Ala Tyr Ser Glu
            100                 105                 110

Glu Arg Asp Arg Pro Tyr Gly Leu Val Ser Ile Asp Thr Val Thr Val
        115                 120                 125

Leu Asp Ala Glu Gly Pro Cys Thr Trp Pro Cys Ser Cys Glu Asp Asp
130                 135                 140

Gly Tyr Pro Ala Leu Asp Leu Asp Ala Gly Leu Glu Pro Ser Pro Gly
145                 150                 155                 160

Leu Glu Asp Pro Leu Leu Asp Ala Gly Thr Thr Val Leu Ser Cys Gly
                165                 170                 175

Cys Val Ser Ala Gly Ser Pro Gly Leu Gly Gly Pro Leu Gly Ser Leu
            180                 185                 190

Leu Asp Arg Leu Lys Pro Pro Leu Ala Asp Gly Glu Asp Trp Ala Gly
        195                 200                 205

Gly Leu Pro Trp Gly Gly Arg Ser Pro Gly Gly Val Ser Glu Ser Glu
    210                 215                 220

Ala Gly Ser Pro Leu Ala Gly Leu Asp Met Asp Thr Phe Asp Ser Gly
225                 230                 235                 240

Phe Val Gly Ser Asp Cys Ser Ser Pro Val Glu Cys Asp Phe Thr Ser
                245                 250                 255

Pro Gly Asp Glu Gly Pro Pro Arg Ser Tyr Leu Arg Gln Trp Val Val
            260                 265                 270

Ile Pro Pro Pro Leu Ser Ser Pro Gly Pro Gln Ala Ser
        275                 280                 285

-continued

```
<210> SEQ ID NO 17
<211> LENGTH: 45
<212> TYPE: PRT
<213> ORGANISM: Artificial Sequence
<220> FEATURE:
<223> OTHER INFORMATION: co-stimulatory domain, NKp30 endodomain

<400> SEQUENCE: 17

Gly Ser Thr Val Tyr Tyr Gln Gly Lys Cys Leu Thr Trp Lys Gly Pro
1               5                   10                  15

Arg Arg Gln Leu Pro Ala Val Val Pro Ala Pro Leu Pro Pro Pro Cys
            20                  25                  30

Gly Ser Ser Ala His Leu Leu Pro Pro Val Pro Gly Gly
        35                  40                  45

<210> SEQ ID NO 18
<211> LENGTH: 63
<212> TYPE: PRT
<213> ORGANISM: Artificial Sequence
<220> FEATURE:
<223> OTHER INFORMATION: co-stimulatory domain, NKp44 endodomain

<400> SEQUENCE: 18

Trp Trp Gly Asp Ile Trp Trp Lys Thr Met Met Glu Leu Arg Ser Leu
1               5                   10                  15

Asp Thr Gln Lys Ala Thr Cys His Leu Gln Gln Val Thr Asp Leu Pro
            20                  25                  30

Trp Thr Ser Val Ser Ser Pro Val Glu Arg Glu Ile Leu Tyr His Thr
        35                  40                  45

Val Ala Arg Thr Lys Ile Ser Asp Asp Asp Glu His Thr Leu
    50                  55                  60

<210> SEQ ID NO 19
<211> LENGTH: 61
<212> TYPE: PRT
<213> ORGANISM: Artificial Sequence
<220> FEATURE:
<223> OTHER INFORMATION: co-stimulatory domain, DNAM-1 (CD226)
      endodomain

<400> SEQUENCE: 19

Asn Arg Arg Arg Arg Glu Arg Arg Asp Leu Phe Thr Glu Ser Trp
1               5                   10                  15

Asp Thr Gln Lys Ala Pro Asn Asn Tyr Arg Ser Pro Ile Ser Thr Ser
            20                  25                  30

Gln Pro Thr Asn Gln Ser Met Asp Asp Thr Arg Glu Asp Ile Tyr Val
        35                  40                  45

Asn Tyr Pro Thr Phe Ser Arg Arg Pro Lys Thr Arg Val
    50                  55                  60

<210> SEQ ID NO 20
<211> LENGTH: 263
<212> TYPE: PRT
<213> ORGANISM: Artificial Sequence
<220> FEATURE:
<223> OTHER INFORMATION: antigen binding domain

<400> SEQUENCE: 20

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30
```

-continued

```
Lys Pro Ser Gln Thr Leu Ser Ile Thr Cys Thr Val Ser Gly Phe Ser
             35                  40                  45

Leu Ala Ser Tyr Asn Ile His Trp Val Arg Gln Pro Pro Gly Lys Gly
 50                  55                  60

Leu Glu Trp Leu Gly Val Ile Trp Ala Gly Gly Ser Thr Asn Tyr Asn
 65                  70                  75                  80

Ser Ala Leu Met Ser Arg Leu Thr Ile Ser Lys Asp Asn Ser Lys Asn
                 85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser
            260

<210> SEQ ID NO 21
<211> LENGTH: 272
<212> TYPE: PRT
<213> ORGANISM: Artificial Sequence
<220> FEATURE:
<223> OTHER INFORMATION: antigen binding domain

<400> SEQUENCE: 21

Met Ala Val Pro Thr Gln Val Leu Gly Leu Leu Leu Leu Trp Leu Thr
 1               5                  10                  15

Asp Ala Arg Cys Asp Ile Gln Met Thr Gln Ser Pro Ser Ser Leu Ser
                 20                  25                  30

Ala Ser Val Gly Asp Arg Val Thr Ile Thr Cys Arg Ala Ser Glu Asp
             35                  40                  45

Ile Tyr Phe Asn Leu Val Trp Tyr Gln Gln Lys Pro Gly Lys Ala Pro
 50                  55                  60

Lys Leu Leu Ile Tyr Asp Thr Asn Arg Leu Ala Asp Gly Val Pro Ser
 65                  70                  75                  80

Arg Phe Ser Gly Ser Gly Ser Gly Thr Gln Tyr Thr Leu Thr Ile Ser
                 85                  90                  95

Ser Leu Gln Pro Glu Asp Phe Ala Thr Tyr Tyr Cys Gln His Tyr Lys
            100                 105                 110

Asn Tyr Pro Leu Thr Phe Gly Gln Gly Thr Lys Leu Glu Ile Lys Arg
        115                 120                 125
```

```
Ser Gly Gly Gly Gly Ser Gly Gly Gly Ser Gly Gly Gly Ser
    130                 135                 140

Gly Gly Gly Gly Ser Arg Ser Glu Val Gln Leu Val Glu Ser Gly Gly
145                 150                 155                 160

Gly Leu Val Gln Pro Gly Gly Ser Leu Arg Leu Ser Cys Ala Ala Ser
                165                 170                 175

Gly Phe Thr Leu Ser Asn Tyr Gly Met His Trp Ile Arg Gln Ala Pro
                180                 185                 190

Gly Lys Gly Leu Glu Trp Val Ser Ile Ser Leu Asn Gly Gly Ser
            195                 200                 205

Thr Tyr Tyr Arg Asp Ser Val Lys Gly Arg Phe Thr Ile Ser Arg Asp
    210                 215                 220

Asn Ala Lys Ser Thr Leu Tyr Leu Gln Met Asn Ser Leu Arg Ala Glu
225                 230                 235                 240

Asp Thr Ala Val Tyr Tyr Cys Ala Ala Gln Asp Ala Tyr Thr Gly Gly
                245                 250                 255

Tyr Phe Asp Tyr Trp Gly Gln Gly Thr Leu Val Thr Val Ser Ser Met
                260                 265                 270

<210> SEQ ID NO 22
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 22

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
    210                 215                 220
```

Ser Leu Ser Leu Ser Pro Gly Lys Lys Asp
225                 230

<210> SEQ ID NO 23
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 23

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 24
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 24

Ala Glu Pro Lys Ser Pro Asp Lys Thr His Thr Cys Pro Pro Cys Pro
1               5                   10                  15

Lys Asp Pro Lys
            20

<210> SEQ ID NO 25
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 25

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 26
<211> LENGTH: 114
<212> TYPE: PRT
<213> ORGANISM: Artificial Sequence
<220> FEATURE:
<223> OTHER INFORMATION: CD3 zeta endodomain

<400> SEQUENCE: 26

Arg Ser Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
                20                  25                  30

Glu Tyr Asp Val Leu Asp Lys Arg Arg Gly Arg Asp Pro Glu Met Gly
            35                  40                  45

Gly Lys Pro Arg Arg Lys Asn Pro Gln Glu Gly Leu Tyr Asn Glu Leu
        50                  55                  60

Gln Lys Asp Lys Met Ala Glu Ala Tyr Ser Glu Ile Gly Met Lys Gly
65                  70                  75                  80

```
Glu Arg Arg Arg Gly Lys Gly His Asp Gly Leu Tyr Gln Gly Leu Ser
            85                  90                  95

Thr Ala Thr Lys Asp Thr Tyr Asp Ala Leu His Met Gln Ala Leu Pro
            100                 105                 110

Pro Arg

<210> SEQ ID NO 27
<211> LENGTH: 4
<212> TYPE: PRT
<213> ORGANISM: Artificial Sequence
<220> FEATURE:
<223> OTHER INFORMATION: activation motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 27

Tyr Xaa Xaa Met
1
```